US012629452B2

(12) United States Patent
Chai et al.

(10) Patent No.: US 12,629,452 B2
(45) Date of Patent: May 19, 2026

(54) CRANIAL SUTURE REGENERATION

(71) Applicant: University of Southern California, Los Angeles, CA (US)

(72) Inventors: Yang Chai, Los Angeles, CA (US); Mengfei Yu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 736 days.

(21) Appl. No.: 18/057,125

(22) Filed: Nov. 18, 2022

(65) Prior Publication Data

US 2023/0158209 A1 May 25, 2023

Related U.S. Application Data

(60) Provisional application No. 63/264,357, filed on Nov. 19, 2021.

(51) Int. Cl.
| | |
|---|---|
| *A61L 27/38* | (2006.01) |
| *A61L 27/22* | (2006.01) |
| *A61L 27/24* | (2006.01) |
| *A61L 27/26* | (2006.01) |
| *A61L 27/36* | (2006.01) |
| *A61L 27/54* | (2006.01) |
| *A61L 27/58* | (2006.01) |

(52) U.S. Cl.
CPC ......... *A61L 27/3834* (2013.01); *A61L 27/222* (2013.01); *A61L 27/227* (2013.01); *A61L 27/24* (2013.01); *A61L 27/26* (2013.01); *A61L 27/3633* (2013.01); *A61L 27/54* (2013.01); *A61L 27/58* (2013.01); *A61L 2300/412* (2013.01)

(58) Field of Classification Search
CPC ... C12N 5/0663; A61L 27/3633; A61L 27/26; A61L 27/24; A61L 27/3834
See application file for complete search history.

(56) References Cited

FOREIGN PATENT DOCUMENTS

| | | | |
|---|---|---|---|
| CA | 3099696 A1 * 11/2019 | ............. | B33Y 80/00 |
| WO | WO-2019094617 A1 * 5/2019 | ............. | A61L 27/54 |
| WO | WO-2019122351 A1 * 6/2019 | ............. | A61L 27/20 |

OTHER PUBLICATIONS

Arbuckle, E.P. et al. "Testing for Odor Discrimination and Habituation in Mice." Journal of Visualized Experiments 99, e52615, 2015.

Bellew, M. et al. "Pre- and postoperative developmental attainment in sagittal synostosis." Arch Dis Child 90, 346-350, 2005.

Bildsoe, H. et al. "Requirement for Twist1 in frontonasal and skull vault development in the mouse embryo." Developmental Biology 331, 176-188, 2009.

Blount, J.P. et al. "Pansynostosis: a review." Childs Nerv. Syst. 23, 1103-1109, 2007.

Bord, S. et al. "Characterization of Osteocrin Expression in Human Bone." Journal of Histochemistry & Cytochemistry 53(10), 1181-1187, 2005.

Brooks, E.D. et al. "The Etiology of Neuronal Development in Craniosynostosis: A Working Hypothesis." The Journal of Craniofacial Surgery vol. 29, No. 1, 49-55, 2018.

Buckley, M.J. et al. "Perirhinal cortical contributions to object perception." Trends in Cognitive Sciences 10, 100-107, 2006.

Cabe, P. A. et al. "A Simple Recording Grip Strength Device." Pharmacology Biochemistry & Behavior, vol. 8, 101-102, 1978.

Chan, C.K.F. et al. "Identification of the Human Skeletal Stem Cell." Cell 175, 43-56, e21, 2018.

Chen, Z.F. et al. "twist is required in head mesenchyme for cranial neural tube morphogenesis." Genes & Development 9, 686-699, 1995.

Collett, B.R. et al. "Attention and executive function in children with and without single-suture craniosynostosis." Child Neuropsychol. 23(1), 83-98, 2017.

Cowan, C.M. et al. "Adipose-derived adult stromal cells heal critical-size mouse calvarial defects." Nature Biotechnology 22, 560-567, 2004.

Gagan, J.R. et al. "Cellular Dynamics and Tissue Interactions of the Dura Mater During Head Development." Birth Defects Research, Part C, 81, 297-304, 2007.

Gompers, A. et al. "Germline Chd8 haploinsufficiency alters brain development in mouse." Nature Neuroscience 20, 8, 1062-1073, 2017.

Gripp, K.W. et al. "Mutations in the Human TWIST Gene." Human Mutation 15, 150-155, 2000.

Guo, Y. et al. (2018). "BMP-IHH-mediated interplay between mesenchymal stem cells and osteoclasts supports calvarial bone homeostasis and repair." Bone Research 6, 30, 2018.

Habeeb, A.F. "Determination of Free Amino Groups in Proteins by Trinitrobenzenesulfonic Acid." Analytical Biochemistry 14, 328-336, 1966.

Ho, T.V. et al. "Integration of comprehensive 3D microCT and signaling analysis reveals differential regulatory mechanisms of craniofacial bone development." Developmental Biology 400, 180-190, 2015.

(Continued)

*Primary Examiner* — Thane Underdahl

(74) *Attorney, Agent, or Firm* — Knobbe, Martens, Olson & Bear, LLP

(57) ABSTRACT

Disclosed herein are compositions of biodegradable scaffolds combined with mesenchymal stem cells and methods of use thereof for the regeneration of cranial sutures and treatment of craniosynostosis, which can help reverse increased intracranial pressure and skull and neurocognitive abnormalities.

20 Claims, 15 Drawing Sheets

(56)                    References Cited

OTHER PUBLICATIONS

Holmes A. et al. "Behavioral profiles of inbred strains on novel, olfactory, spatial and emotional tests for reference memory in mice." Genes, Brain and Behavior 1, 55-69, 2002.

Holmes A. et al. "Evaluation of an Anxiety-Related Phenotype in Galanin Overexpressing Transgenic Mice." Journal of Molecular Neuroscience, vol. 18, 151-165, 2002.

James, A.W. et al. "Proliferation, Osteogenic Differentiation, and FGF-2 Modulation of Posterofrontal/Sagittal Suture-Derived Mesenchymal Cells In Vitro." Plastic and Reconstructive Surgery, vol. 122, No. 1, 53-63, 2008.

Kabbani, H. et al. "Craniosynostosis." American Family Physician, 69, 2863-2870, 2004.

Kaemmerer, E. et al. "Gelatine methacrylamide-based hydrogels: An alternative three-dimensional cancer cell culture system." Acta Biomaterial 10, 2551-2562, 2014.

Kang, M. et al. "Simplified Equation to Extract Diffusion Coefficients from Confocal FRAP Data." Traffic 13, 1589-1600, 2013.

Kilcoyne, S. et al. "Language Development, Hearing Loss, and Intracranial Hypertension in Children With TWIST1-Confirmed Saethre-Chotzen Syndrome." The Journal of Craniofacial Surgery vol. 30, No. 5,1506-1511, 2019.

Klingenberg, C.P. "MorphoJ: an integrated software package for geometric morphometrics." Molecular Ecolology Resources, 11, 353-357, 2011.

Krueger, F. et al. "The medial prefrontal cortex mediates social event knowledge." Trends in Cognitive Science, vol. 13, No. 3, 103-109, 2009.

Kwan, M.D. et al. "Microarray Analysis of the Role of Regional Dura Mater in Cranial Suture Fate." Plastic and Reconstructive Surgery, vol. 122, No. 2, 389-399, 2008.

Lane, L.C. "Pioneer Craniectomy for Relief of Mental Imbecility Due to Premature Sutural Closure and Microcephalus." JAMA 18, 49-50, 1892.

Leger, M. et al. "Object recognition test in mice." Nature Protocols, vol. 8, No. 12, 2531-2537, 2013.

Leone D.P. et al. "The determination of projection neuron identity in the developing cerebral cortex." Curr Opin Neurobiol. 18(1), 28-35, 2008.

Liu, H. et al. "microRNA-203 promotes proliferation, differentiation, and migration of osteoblasts by upregulation of Msh homeobox 2." J. Cell Physiol. 234, 17639-17648, 2019.

Liu, Y. et al. "Mesenchymal Stem Cell-Based Tissue Regeneration is Governed by Recipient T Lymphocytes via IFN-gamma and TNF-alpha." Nat. Med. 17(12),1594-1601, 2012.

Mao, J.J. et al. "Craniofacial Tissue Engineering by Stem Cells." J. Dent. Res., 85(11), 966-979, 2006.

Maruyama, T. et al. "Stem cells of the suture mesenchyme in craniofacial bone development, repair and regeneration." Nature Communications, 7, 10526, 2016.

Millichap, J.G. "Cognitive Development of Children with Craniosynostosis." Pediatric Neurolology Briefs, vol. 29, No. 6, 47, 2015.

Molyneaux B.J. et al. "Neuronal subtype specification in the cerebral cortex." Nature Reviews Neuroscience, vol. 8, 427-437, 2007.

Morriss-Kay, G.M. et al. "Growth of the normal skull vault and its alteration in craniosynostosis: insights from human genetics and experimental studies." J. Anat. 207, 637-653, 2005.

Murtha, L. et al. "Epidural Intracranial Pressure Measurement in Rats Using a Fiber-optic Pressure Transducer." Journal of Visualized Experiments, 62, e3689, 2012.

Noshadi, I. et al. "In vitro and in vivo analysis of visible light crosslinkable gelatin methacryloyl (GelMA) hydrogels." Biomaterials Science, 5, 2093-2105, 2017.

Ogle, R.C. et al. "Regulation of Cranial Suture Morphogenesis." Cells Tissues Organs, 176, 54-66, 2004.

Park, S. et al. "Sutures Possess Strong Regenerative Capacity for Calvarial Bone Injury." Stem Cells and Development vol. 25, No. 23,1801-1807, 2016.

Parsons, T.E. et al. "Craniofacial Shape Variation in Twist1+/ −Mutant Mice." The Anatatomical Record 297, 826-833, 2014.

Reardon, W. et al. "Craniosynostosis associated with FGFR3 pro250arg mutation results in a range of clinical presentations including unisutural sporadic craniosynostosis." J. Med. Genet., 34, 632-636, 1997.

Renier, D. et al. "Intracranial pressure in craniostenosis." J. Neurosurg. vol. 57, 370-377, 1982.

Rinaldi, T. et al. "Hyper-connectivity and hyper-plasticity in the medial prefrontal cortex in the valproic acid animal model of autism." Frontiers in Neural Circuits, vol. 2, Art. 4, 2008.

Semple, B.D. et al. "Brain development in rodents and humans: Identifying benchmarks of maturation and vulnerability to injury across species." Progress in Neurobiology, 1-16, 2013.

Shin, L. et al. "Human Mesenchymal Stem Cell Grafts Enhance Normal and Impaired Wound Healing by Recruiting Existing Endogenous Tissue Stem/Progenitor Cells." Stem Cells Translational Medicine, 2, 33-42, 2013.

Shim, K.W. et al. "Neurodevelopmental Problems in Non-Syndromic Craniosynostosis." J. Korean Neurosurg. Soc. 59(3), 242-246, 2016.

Sidoti, E.J., Jr. et al. "Long-Term Studies of Metopic Synostosis: Frequency of Cognitive Impairment and Behavioral Disturbances." Plastic and Reconstructive Surgery, vol. 97, No. 2, 276-281, 1996.

Smith, J. P. et al. "Quantitative measurement of muscle strength in the mouse." Journal of Neuroscience Methods 62, 15-19, 1995.

Speltz, M.L. et al. "Intellectual and Academic Functioning of School-Age Children with Single-Suture Craniosynostosis." Pediatrics vol. 135, No. 3, e615-623, 2015.

Sun, A.H. et al. "An Investigation of Brain Functional Connectivity by Form of Craniosynostosis." J. Craniofac. Surg., 30(6), 1719-1723, 2019.

Sousa, A. M. M. et al. "Molecular and Cellular Reorganization of Neural Circuits in the Human Lineage." Science, 358(6366), 1027-1032, 2017.

Twigg, et al. "A Genetic-Pathophysiological Framework for Craniosynostosis." The American Journal of Human Genetics, 97, 359-377, 2015.

Van Den Bulcke, A.I. et al. "Structural and Rheological Properties of Methacrylamide Modified Gelatin Hydrogels." Biomacromolecules, vol. 1, No. 1, 31-38, 2000.

Wallace, E.R. et al. "Visuomotor function in school-age children with single-suture craniosynostosis." J. Dev. Behav. Pediatr., 37(6), 483-490, 2016.

Wolfswinkel, E.M. et al. "Is Postoperative Intensive Care Unit Care Necessary following Cranial Vault Remodeling for Sagittal Synostosis?" Plastic and Reconstructive Surgery, 140, 1235-1239, 2017.

Xing, J. et al. "Inflammatory Microenvironment Changes the Secretory Profile of Mesenchymal Stem Cells to Recruit Mesenchymal Stem Cells." Cell Physiololgy and Biochemistry, 33, 905-919, 2014.

Xu, X. et al. "PDGFR-alpha signaling is critical for tooth cusp and palate morphogenesis." Developmental Dynamics, vol. 232, Issue 1, 75-84, 2005.

Yu, H.M. et al. "The role of Axin2 in calvarial morphogenesis and craniosynostosis." Development, 132, 1995-2005, 2005.

Zechi-Ceide, R.M. et al. "Saethre-Chotzen Phenotype With Learning Disability and Hyper IgE Phenotype in a Patient Due to Complex Chromosomal Rearrangement Involving Chromosomes 3 and 7." American Journal of Medical Genetics, 158A, 1680-1685, 2012.

Zhao, H. et al. "Stem Cells in Teeth and Craniofacial Bones." Journal of Dental Research vol. 94(11), 1495-1501, 2015.

Zhao, H. et al. "The suture provides a niche for mesenchymal stem cells of craniofacial bones." Nature Cell Biology, vol. 17, No. 4, 386-396, 2015.

Zhu, Y. et al. "Spatiotemporal transcriptomic divergence across human and macaque brain development." Science, 362, published online Epub Dec. 14, (10.1126/science.aat8077) 2018.

* cited by examiner

CRANIAL SUTURE REGENERATION

CROSS-REFERENCE TO RELATED APPLICATION

This application claims priority to U.S. Provisional Patent Application 63/264,357, filed Nov. 19, 2021, the entire contents of which is incorporated by reference herein.

STATEMENT REGARDING FEDERALLY SPONSORED R&D

This invention was made with government support under Grant Nos. DE026339 and DE012711 awarded by the National Institutes of Health (NIH). The government has certain rights to the invention.

FIELD

Aspects of the present disclosure relate to compositions comprising a biodegradable scaffold and mesenchymal stem cells. This disclosure also relates to such compositions that may be applied to calvarial defects for cranial suture regeneration.

BACKGROUND

Craniosynostosis is a common disorder in which one or more calvarial sutures, the fibrous joints that separate the skull bones, fuse prematurely in infancy. This causes abnormal skull growth, increased intracranial pressure (ICP), delayed brain development, and often impaired cognitive functions. Calvarial suture patency is crucial for allowing the skull to compress during childbirth and accommodating its extensive postnatal growth in concert with the developing brain, which continues into adulthood.

Patients with craniosynostosis often exhibit neurocognitive dysfunctions and intellectual disabilities. For example, patients with Saethre-Chotzen syndrome have mutations in TWIST1 and show preferential loss of the coronal suture. Large deletions including the TWIST1 locus have been associated with learning disabilities and neurocognitive impairment. Gain-of-function mutations in ZIC1 or FGFR lead to craniosynostosis and learning disabilities. Although neurocognitive deficits are more commonly associated with syndromic craniosynostosis, some patients with nonsyndromic single-suture craniosynostosis may develop intellectual disability and developmental delays that vary in severity. These studies highlight the heterogeneity of these deficits and provide evidence that craniosynostosis alone may cause neurocognitive dysfunction. Overall, premature suture fusion can adversely impact neurocognition, likely due to increased ICP and neuroanatomical changes.

Currently, the only treatment for craniosynostosis is complex surgery to correct the skull deformity and prevent its sequelae. In many cases, the bones resynostose, necessitating re-operation. There is an immense need for better treatment of craniosynostosis and prevention of resynostosis.

RELATED ART REFERENCES

The following publications are related art for the background of this disclosure.

Arbuckle, E. P., Smith, G. D., Gomez, M. C., and Lugo, J. N. (2015). Testing for Odor Discrimination and Habituation in Mice. J. Vis. Exp. 99, e52615.

Bellew, M., Chumas, P., Mueller, R., Liddington, M., and Russell, J. (2005). Pre- and postoperative developmental attainment in sagittal synostosis. Arch Dis Child. 90, 346-350.

Bildsoe, H., Loebel, D. A., Jones, V. J., Chen, Y. T., Behringer, R. R., and Tam, P. P. (2009). Requirement for Twist1 in frontonasal and skull vault development in the mouse embryo. Dev Biol. 331, 176-188.

Blount, J. P., Louis, R. G., Tubbs, R. S., and Grant, J. H. (2007). Pansynostosis: a review. Childs Nerv. Syst. 23, 1103-1109.

Bord, S., Ireland, D. C., Moffatt, P., Thomas, G. P., and Compston, J. E. (2005). Characterization of osteocrin expression in human bone. J. Histochem. Cytochem. 53, 1181-1187.

Brooks, E. D., Beckett, J. S., Yang, J., Timberlake, A. T., Sun, A. H., Chuang, C., and Persing, J. A. (2018). The Etiology of Neuronal Development in Craniosynostosis: A Working Hypothesis. J. Craniofac. Surg. 29, 49-55.

Buckley, M. J., and Gaffan, D. (2006). Perirhinal cortical contributions to object perception. Trends Cogn. Sci. 10, 100-107.

Cabe, P. A., Tilson, H. A., Mitchell, C. L. and Dennis, R. (1978). A simple recording grip strength device. Pharmacol. Biochem. Behav. 8, 101-102.

Chan, C. K. F., Gulati, G. S., Sinha, R., Tompkins, J. V., Lopez, M., Carter, A. C., Ransom, R. C., Reinisch, A., Wearda, T., Murphy, M., et al. (2018). Identification of the Human Skeletal Stem Cell. Cell 175, 43-56 e21.

Chen, Z. F., and Behringer, R. R. (1995). Twist is required in head mesenchyme for cranial neural tube morphogenesis. Genes Dev. 9, 686-699.

Collett, B. R., Kapp-Simon, K. A., Wallace, E., Cradock, M. M., Buono, L., and Speltz M. L. (2017). Attention and executive function in children with and without single-suture craniosynostosis. Child Neuropsychol. 23, 83-98.

Cowan, C. M., Shi, Y. Y., Aalami, O. O., Chou, Y. F., Mari, C., Thomas, R., Quarto, N., Contag, C. H., Wu, B., and Longaker, M. T. (2004). Adipose-derived adult stromal cells heal critical-size mouse calvarial defects. Nat. biotechnol. 22, 560-567.

Gagan, J. R., Tholpady, S. S., and Ogle, R. C. (2007). Cellular dynamics and tissue interactions of the dura mater during head development. Birth defects Res. C. Embryo Today 81, 297-304.

Gompers, A., Su-Feher, L., Ellegood, J., Copping, N. A., Riyadh, M. A., Stradleigh, T. W., Pride, M. C., Schaffler, M. D., Wade, A. A., Catta-Preta, R., et al. (2017). Germline Chd8 haploinsufficiency alters brain development in mouse. Nat Neurosci. 20, 1062-1073

Gripp, K. W., Zackai, E. H., and Stolle, C. A. (2000). Mutations in the human TWIST gene. Hum. Mutat. 15, 479.

Guo, Y., Yuan, Y., Wu, L., Ho, T. V., Jing, J., Sugii, H., Li, J., Han, X., Feng, J., Guo, C., and Chai, Y. (2018). BMP-IHH-mediated interplay between mesenchymal stem cells and osteoclasts supports calvarial bone homeostasis and repair. Bone Res. 6, 30.

Habeeb, A. F. (1966). Determination of free amino groups in proteins by trinitrobenzenesulfonic acid. Anal.Biochem. 14, 328-336.

Ho, T. V., Iwata, J., Ho, H. A., Grimes, W. C., Park, S., Sanchez-Lara, P. A., and Chai, Y. (2015). Integration of comprehensive 3D microCT and signaling analysis reveals differential regulatory mechanisms of craniofacial bone development. Dev. Biol. 400, 180-190.

Holmes A., Wrenn C. C., Harris A. P., Thayer K., and Crawley J. N. (2002a). Behavioral profiles of inbred strains on novel, olfactory, spatial and emotional tests for reference memory in mice. Genes Brain Behav. 1:55-69.

Holmes A., Yang R. J., and Crawley J. N. (2002b). Evaluation of an anxiety-related phenotype in galanin overexpressing transgenic mice. J. Mol. Neurosci. 18:151-165.

James, A. W., Xu, Y., Wang, R., and Longaker, M. T. (2008). Proliferation, osteogenic differentiation, and fgf-2 modulation of posterofrontal/sagittal suture-derived mesenchymal cells in vitro. Plast. Reconstr. Surg.122, 53-63.

Kabbani, H., and Raghuveer, T. S. (2004). Craniosynostosis. Am. Fam. Physician. 69, 2863-2870.

Kaemmerer, E., Melchels, F. P., Holzapfel, B. M., Meckel, T., Hutmacher, D. W., and Loessner, D. (2014). Gelatinemethacrylamide-based hydrogels: an alternative three-dimensional cancer cell culture system. Acta. Biomater. 10, 2551-2562.

Kang, M., Day, C. A., Kenworthy, A. K., and DiBenedetto, E. (2013). Simplified equation to extract diffusion coefficients from confocal FRAP data. Traffic 13, 1589-1600.

Kilcoyne, S., Luscombe, C., Scully, P., Jayamohan, J., Magdum, S., Wall, S., Johnson, D., and Wilkie, A. O. M. (2019). Language Development, Hearing Loss, and Intracranial Hypertension in Children With TWIST1-Confirmed Saethre-Chotzen Syndrome. J. Craniofac. Surg. 30, 1506-1511.

Klingenberg, C. P. (2011). MorphoJ: an integrated software package for geometric morphometrics. Mol. Ecol. Resour. 11, 353-357.

Krueger, F., Barbey, A. K., and Grafman, J. (2009). The medial prefrontal cortex mediates social event knowledge. Trends Cogn. Sci. 13, 103-109.

Kwan, M. D., Wan, D. C., Wang, Z., Gupta, D. M., Slater, B. J., and Longaker, M. T. (2008). Microarray analysis of the role of regional dura mater in cranial suture fate. Plast. Reconstr. Surg. 122, 389-399.

Lane, L. C. (1892). Pioneer Craniectomy for Relief of Mental Imbecility Due to Premature Sutural Closure and Microcephalus. JAMA 18, 49-50.

Leger, M., Quiedeville, A., Bouet, V., Haelewyn, B., Boulouard, M., Schumann-Bard, P., and Freret, T. (2013). Object recognition test in mice. Nat. Protoc.8, 2531-2537.

Leone D. P., Srinivasan K., Chen B., Alcamo E., and McConnell S. K. (2008). The determination of projection neuron identity in the developing cerebral cortex. Curr Opin Neurobiol. 18, 28-35.

Liu, H., Chen, B., and Li, Y. (2019). microRNA-203 promotes proliferation, differentiation, and migration of osteoblasts by upregulation of Msh homeobox 2. J. Cell Physiol. 234, 17639-17648.

Liu, Y., Wang, L., Kikuiri, T., Akiyama, K., Chen, C., Xu, X., Yang, R., Chen, W., Wang, S., and Shi, S. (2011). Mesenchymal stem cell-based tissue regeneration is governed by recipient T lymphocytes via IFN-gamma and TNF-alpha. Nat. Med. 17, 1594-1601.

Mao, J. J., Giannobile, W. V., Helms, J. A., Hollister, S. J., Krebsbach, P. H., Longaker, M. T., and Shi, S. (2006). Craniofacial tissue engineering by stem cells. J. Dent. Res. 85, 966-979.

Maruyama, T., Jeong, J., Sheu, T. J., and Hsu, W. (2016). Stem cells of the suture mesenchyme in craniofacial bone development, repair and regeneration. Nat. Commun. 7, 10526.

Millichap, J. G. (2015). Cognitive Development of Children with Craniosynostosis. Pediatr. Neurol. Briefs 29, 47.

Molyneaux B. J., Arlotta P., Menezes J. R., and Macklis J. D. (2007). Neuronal subtype specification in the cerebral cortex. Nat Rev Neurosci. 8, 427-437.

Morriss-Kay, G. M., and Wilkie, A. O. (2005). Growth of the normal skull vault and its alteration in craniosynostosis: insights from human genetics and experimental studies. J. Anat. 207, 637-653.

Murtha, L., McLeod, D., and Spratt, N. (2012). Epidural intracranial pressure measurement in rats using a fiber-optic pressure transducer. J. Vis. Exp. 62, e3689

Noshadi, I., Hong, S., Sullivan, K. E., Shirzaei Sani, E., Portillo-Lara, R., Tamayol, A., Shin, S. R., Gao, A. E., Stoppel, W. L., Black, L. D., III, Khademhosseini, A., and Annabi, N. (2017). In vitro and in vivo analysis of visible light crosslinkable gelatin methacryloyl (GelMA) hydrogels. Biomater.Sci. 5, 2093-2105.

Ogle, R. C., Tholpady, S. S., McGlynn, K. A., and Ogle, R. A. (2004). Regulation of cranial suture morphogenesis. Cells Tissues Organs 176, 54-66.

Park, S., Zhao, H., Urata, M., and Chai, Y. (2016). Sutures Possess Strong Regenerative Capacity for Calvarial Bone Injury. Stem Cells Dev. 25, 1801-1807.

Parsons, T. E., Weinberg, S. M., Khaksarfard, K., Howie, R. N., Elsalanty, M., Yu, J. C., and Cray, J. J. (2014). Craniofacial shape variation in Twist1+/− mutant mice. Anat. Rec. 297, 826-833.

Reardon, W., Wilkes, D., Rutland, P., Pulleyn, L. J., Malcolm, S., Dean, J. C., Evans, R. D., Jones, B. M., Hayward, R., Hall, C. M., et al. (1997). Craniosynostosis associated with FGFR3 pro250arg mutation results in a range of clinical presentations including unisutural sporadic craniosynostosis. J. Med. Genet. 34, 632-636.

Renier, D., Sainte-Rose, C., Marchac, D., and Hirsch, J. F. (1982). Intracranial pressure in craniostenosis. J. Neurosurg.57, 370-377.

Rinaldi, T., Perrodin, C., and Markram, H. (2008). Hyper-connectivity and hyper-plasticity in the medial prefrontal cortex in the valproic Acid animal model of autism. Front. Neural Circuits 2, 4.

Semple, B. D., Blomgren, K., Gimlin, K., Ferriero, D. M., and Noble-Haeusslein, L. J. (2013). Brain development in rodents and humans: Identifying benchmarks of maturation and vulnerability to injury across species. Prog. Neurobiol. 106-107, 1-16.

Shin, L., and Peterson, D. A. (2013). Human mesenchymal stem cell grafts enhance normal and impaired wound healing by recruiting existing endogenous tissue stem/progenitor cells. Stem Cells Transl. Med. 2, 33-42.

Shim, K. W., Park, E. K., Kim, J. S., Kim, Y. O., and Kim, D. S. (2016). Neurodevelopmental Problems in Non-Syndromic Craniosynostosis. J. Korean Neurosurg. Soc. 59, 242-246.

Sidoti, E. J., Jr., Marsh, J. L., Marty-Grames, L., and Noetzel, M. J. (1996). Long-term studies of metopic synostosis: frequency of cognitive impairment and behavioral disturbances. Plast. Reconstr. Surg. 97, 276-281.

Smith, J. P., Hicks, P. S., Ortiz, L. R., Martinez, M. J. and Mandler, R. N. (1995). Quantitative measurement of muscle strength in the mouse. J. Neurosci. Methods 62, 15-19.

Speltz, M. L., Collett, B. R., Wallace, E. R., Starr, J. R., Cradock, M. M., Buono, L., Cunningham, M., and Kapp-Simon, K. (2015). Intellectual and academic functioning of school-age children with single-suture craniosynostosis. Pediatrics 135, e615-623.

Sun, A. H., Eilbott, J., Chuang, C., Yang, J. F., Brooks, E. D., Beckett, J., Steinbacher, D. M., Pelphrey, K., and Persing, J. A. (2019). An Investigation of Brain Functional Connectivity by Form of Craniosynostosis. J. Craniofac. Surg.30, 1719-1723.

Sousa, A. M. M., Zhu, Y., Raghanti, M. A., Kitchen, R. R., Onorati, M., Tebbenkamp, A. T. N., Stutz, B., Meyer, K. A., Li, M., Kawasawa, Y. I., Liu, F., et al., (2017) Molecular and cellular reorganization of neural circuits in the human lineage. Science, 358, 1027-1032.

Twigg, S. R., and Wilkie, A. O. (2015). A Genetic-Pathophysiological Framework for Craniosynostosis. Am. J. Hum. Genet. 97, 359-377.

Van Den Bulcke, A. I., Bogdanov, B., De Rooze, N., Schacht, E. H., Cornelissen, M., and Berghmans, H. (2000). Structural and rheological properties of methacrylamide modified gelatin hydrogels. Biomacromolecules 1, 31-38.

Visuomotor Function in School-Age Children with Single-Suture Craniosynostosis. J. Dev. Behav. Pediatr. 37, 483-490.

Wallace, E. R., Collett, B. R., Kapp-Simon, K., Starr, J. R., Birgfeld, C., and Speltz, M. L. (2016).

Wolfswinkel, E. M., Howell, L. K., Fahradyan, A., Azadgoli, B., McComb, J. G., and Urata, M. M. (2017). Is Postoperative Intensive Care Unit Care Necessary following Cranial Vault Remodeling for Sagittal Synostosis? Plast. Reconstr. Surg.140, 1235-1239.

Xing, J., Hou, T., Jin, H., Luo, F., Change, Z., Li, Z., Xie, Z., and Xu, J. (2014). Inflammatory microenvironment changes the secretory profile of mesenchymal stem cells to recruit mesenchymal stem cells. Cell Physiol. Biochem. 33, 905-919.

Xu, X., Bringas, P. Jr., Soriano, P., and Chai, Y. (2005). PDGFR-alpha signaling is critical for tooth cusp and palate morphogenesis. Dev.Dyn. 232, 75-84.

Yu, H. M., Jerchow, B., Sheu, T. J., Liu, B., Costantini, F., Puzas, J. E., Birchmeier, W., and Hsu, W. (2005). The role of Axin2 in calvarial morphogenesis and craniosynostosis. Development 132, 1995-2005.

Zechi-Ceide, R. M., Rodrigues, M. G., Jehee, F. S., Kokitsu-Nakata, N. M., Passos-Bueno, M. R., and Guion-Almeida, M. L. (2012). Saethre-Chotzen phenotype with learning disability and hyper IgE phenotype in a patient due to complex chromosomal rearrangement involving chromosomes 3 and 7. Am. J. Med. Genet. A. 158A, 1680-1685.

Zhao, H., and Chai, Y. (2015). Stem Cells in Teeth and Craniofacial Bones. J. Dent. Res. 94, 1495-1501.

Zhao, H., Feng, J., Ho, T. V., Grimes, W., Urata, M., and Chai, Y. (2015). The suture provides a niche for mesenchymal stem cells of craniofacial bones. Nat. Cell Biol. 17, 386-396.

Zhu, Y., Sousa, A. M. M., Gao, T., Skarica, M., Li, M., Santpere, G., Esteller-Cucala, P., Juan, D., Ferrández-Peral, L., Gulden, F. O. et al., (2018) Spatiotemporal transcriptomic divergence across human and macaque brain development. Science, 362, published online Epub December 14 (10.1126/science.aat8077).

The entire content of each of the above publications is incorporated herein by reference.

SUMMARY

This disclosure relates to compositions and methods that may be used regeneration of cranial sutures and treatment of craniosynostosis, which can help reverse increased intracranial pressure and skull and neurocognitive abnormalities.

Craniosynostosis results from premature fusion of the cranial suture(s), which contain mesenchymal stem cells (MSCs) that are crucial for calvarial expansion in coordination with brain growth. Infants with craniosynostosis have skull dysmorphology, increased intracranial pressure, and complications such as neurocognitive impairment that compromise quality of life. Animal models recapitulating these phenotypes are lacking, hampering the development of urgently needed innovative therapies.

As shown herein, Twist1$^{+/-}$ mice with craniosynostosis have increased intracranial pressure and neurocognitive behavioral abnormalities, recapitulating features of human Saethre-Chotzen syndrome. As also disclosed herein, use of a biodegradable material combined with MSCs is able to successfully regenerate a functional cranial suture that corrects skull deformity, normalizes intracranial pressure, and rescues neurocognitive behavior deficits. The regenerated suture creates a niche into which endogenous MSCs migrate, sustaining calvarial bone homeostasis and repair. MSC-based cranial suture regeneration offers a paradigm shift in treatment to reverse skull and neurocognitive abnormalities in this devastating disease.

In this disclosure, the composition, which may be used for regeneration of cranial sutures and treatment of craniosynostosis, may include methacrylated gelatin (GelMA), extracellular matrix (for example, Matrigel), and collagen I. This composition may further include Gli1+ mesenchymal stem cells.

In this disclosure, Gli1+ mesenchymal stem cells may be suspended in the composition at a density, expressed in a number of cells per milliliter (mL) of the composition, in a range of $0.1 \times 10^7$ cells/mL to $50 \times 10^7$ cells/mL, or in a range of $1 \times 10^7$ cells/mL to $20 \times 10^7$ cells/mL, or in a range of $2 \times 10^7$ cells/mL to $10 \times 10^7$ cells/mL, or in a range of $3 \times 10^7$ cells/mL to $7 \times 10^7$ cells/mL. The said density may also be about $5 \times 10^7$ cells/mL.

In this disclosure, GelMA in the composition may be at a concentration, expressed in percent weight (w) of GelMa per volume (v) of the composition, in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v. The said concentration may also be in a range of 3.8% w/v to 3.9% w/v.

In this disclosure, extracellular matrix in the composition may be at a concentration, expressed in percent volume (v) of extracellular matrix per volume (v) of the composition, in a range of 1% v/v to 30% v/v, or in a range of 10% v/v to 20% v/v, or in a range of 13% v/v to 17% v/v, or in a range of 14% v/v to 16% v/v. The said concentration may also be about 15% v/v.

In this disclosure, collagen I in the composition may be at a concentration, expressed in a microgram (µg) of collagen I in per milliliter (mL) of the composition, in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.

This disclosure also relates to a method of treating a calvarial defect and/or regenerating a cranial suture in a patient by administering any composition of this disclosure to the calvarial defect, and exposing the composition to ultraviolet light to crosslink the composition in contact with the calvarial defect. The patient may be a human. The calavarial defect may be intentionally generated surgically to a fused cranial suture. The method of treatment may be used to treat craniosynostosis. The composition, for example, may include methacrylated gelatin (GelMA), extracellular matrix, collagen I, and Gli1+ mesenchymal stem cells. The composition, for example, may include methacrylated gelatin (GelMA), and extracellular matrix, collagen I. GelMA in such compositions, for example, may at a concentration in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v. Extracellular matrix in such compositions may be at a concentration in a range of 1% v/v to 30% v/v, or in a range of 10% v/v to 20% v/v, or in a range of 13% v/v to 17% v/v, or in a range of 14% v/v to 16% v/v. Collagen I in such compositions may be at a concentration of in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL. Gli1+ mesenchymal stem cells may be suspended in the composition at a density, expressed in a number of cells per milliliter (mL) of the composition, in a range of $0.1\times10^7$ cells/mL to $50\times10^7$ cells/mL, or in a range of $1\times10^7$ cells/mL to $20\times10^7$ cells/mL, or in a range of $2\times10^7$ cells/mL to $10\times10^7$ cells/mL, or in a range of $3\times10^7$ cells/mL to $7\times10^7$ cells/mL.

Embodiments of the present disclosure provided herein may also be described by way of the following numbered alternatives or examples:

1. A composition comprising methacrylated gelatin (GelMA), extracellular matrix, collagen I, and Gli1+ mesenchymal stem cells.
2. The composition of alternative 1, wherein Gli1+ mesenchymal stem cells are suspended in the composition at a density in a range of $0.1\times10^7$ cells/mL to $50\times10^7$ cells/mL, or in a range of $1\times10^7$ cells/mL to $20\times10^7$ cells/mL, or in a range of $2\times10^7$ cells/mL to $10\times10^7$ cells/mL, or in a range of $3\times10^7$ cells/mL to $7\times10^7$ cells/mL.
3. The composition of alternative 1, wherein GelMA in the composition is at a concentration in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v.
4. The composition of alternative 2, wherein GelMA in the composition is at a concentration in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v.
5. The composition of alternative 1, wherein extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v.
6. The composition of alternative 2, wherein extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v.
7. The composition of alternative 3, wherein extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v.
8. The composition of alternative 4, wherein extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v.
9. The composition of alternative 1, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
10. The composition of alternative 2, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
11. The composition of alternative 3, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
12. The composition of alternative 4, wherein collagen I in the composition is at a concentration of in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
13. The composition of alternative 5, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
14. The composition of alternative 6, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
15. The composition of alternative 7, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
16. The composition of alternative 8, wherein collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
17. A composition comprising methacrylated gelatin (GelMA), extracellular matrix, and collagen I.
18. The composition of claim 17; wherein:
GelMA in the composition is at a concentration in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v; and
extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v; and
collagen I in the composition is at a concentration in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL.
19. A method of treating a calvarial defect and/or regenerating a cranial suture in a patient, comprising: administering the composition of claim 1 to the calvarial defect, and exposing the composition to ultraviolet light to crosslink the composition in contact with the calvarial defect.

20. The method of claim 19, wherein:

GelMA in the composition is at a concentration in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v; and extracellular matrix in the composition is at a concentration in a range of 1% v/v to 30% v/v, or in a range of 10% v/v to 20% v/v, or in a range of 13% v/v to 17% v/v, or in a range of 14% v/v to 16% v/v; and collagen I in the composition is at a concentration of in a range of 100 µg/mL to 400 µg/mL, or in a range of 200 µg/mL to 300 µg/mL, or in a range of 210 µg/mL to 260 µg/mL, or in a range of 220 µg/mL to 250 µg/mL; and Gli1+ mesenchymal stem cells are suspended in the composition at a density in a range of $0.1 \times 10^7$ cells/mL to $50 \times 10^7$ cells/mL, or in a range of $1 \times 10^7$ cells/mL to $20 \times 10^7$ cells/mL, or in a range of $2 \times 10^7$ cells/mL to $10 \times 10^7$ cells/mL, or in a range of $3 \times 10^7$ cells/mL to $7 \times 10^7$ cells/mL.

Any combination of above features, variations, examples, alternatives, or embodiments is within the scope of this disclosure.

BRIEF DESCRIPTION OF THE DRAWINGS

FIG. 1A shows a diagram depicting the intracranial pressure measurement step. FIG. 1B-C show representative intracranial pressure (ICP) traces (FIG. 1B) and quantification (FIG. 1C) of ICP values (wild type (WT), n=8; Twist1$^{+/-}$ with bilateral suture fusion (MUT), n=6 mice). FIG. 1D shows a schematic of a rotarod test. FIG. 1E shows rotarod performance scored as time (seconds on the rotarod). FIG. 1F depicts a schematic of a novel object test. FIG. 1G depicts representative animal tracks in the novel object test. FIG. 1H shows preference indices in the novel object test. FIG. 1I shows a schematic for a three chamber test. FIG. 1J depicts representative animal tracks in the three chamber test. FIG. 1K shows preference indices in sociability and social novelty tests. (WT, n=20; MUT, n=20). Data are mean±s.e.m. *P<0.05, P<0.01, *P<0.001, ****P<0.0001, NS, not significant calculated by two-tailed unpaired t-test.

FIG. 2A-N depicts data showing that suture MSCs and modified methacrylated gelatin (M-GM) can support the regeneration of a cranial suture. FIG. 2A-F shows an overview of the calvarial surgery showing the calvaria before surgery (FIG. 2A, C) and after surgery (FIG. B, D). MicroCT of calvaria (FIG. 2C-D). White arrowheads indicate the residual hallmark of the fused suture (FIG. 2A, C, D). The defect on one side of the calvaria was filled with pure M-GM or left empty as a control, and the defect on the other side was filled with M-GM plus Gli1$^+$ cells (FIG. 2E-F). Scale bar, 2 mm. FIG. 2G-L show MicroCT images (3-D reconstruction and slice) for controls (Panels G1, I1, K1 for blank, and Panels H1, J1, L1 for pure M-GM) and M-GM plus suture MSCs (M-GM+SCs; Panels H2, J2, L2) at one, three, and six months post-surgery. Dotted lines (white) outline the original surgical defects. Scale bar, 2 mm. FIG. 2M shows HE staining of blank control (left), M-GM (middle) and M-GM+SC (right) groups at one, three, and six months post-surgery. Outlined areas in M-GM+SC group are separately shown in right panels. Black arrowheads indicate the positions of initial defects, and asterisk shows suture-like structure in M-GM+SCs six months post-surgery. Scale bar, 200 µm. FIG. 2N shows immunofluorescence staining for M-GM+SCs at one month (left), three months (middle), and six months post-surgery (right). Red fluorescently labeled cells were harvested from one-month-old Gli1-Cre$^{ERT2}$; tdT$^{fl/+}$ mice. White arrowheads indicate donor cells (red) in surrounding tissues; white dotted lines show boundaries of bones. Scale bar, 200 µm in upper panel; 25 µm in lower panel.

FIG. 3A-D shows Qtracker FITC labeled dura mater cells migrate from the dura at day 0 (FIG. 3A) to the regenerated suture at four weeks post-surgery (FIG. 3B-D). Donor cells fluorescently labeled in red were harvested from one-month-old Gli1-Cre$^{ERT2}$;tdT$^{fl/+}$ mice. Gli1$^+$ cells were labeled with Alexa-647 and arrowheads indicate the co-labeled signals (FIG. 3C-D). Scale bar, 50 µm in inset in (FIG. 3A), 200 µm in (FIG. 3A); 100 µm in (FIG. 3B); 50 µm in (FIG. 3D). FIG. 3E shows a schematic of dura mater blockage surgery. FIG. 3F shows MicroCT images (3-D reconstruction and slice), HE and immunofluorescence staining of the defects six weeks post-dura mater blocking. Black dotted lines in (FIG. 3F) outline the original surgical defects. (Panels F2, F3) Asterisks indicate the Parafilm membrane (yellow dotted lines in Panel F3); arrowheads indicate the dura mater. Scale bars, 500 µm in (FIG. 3F) and (Panel F1); 100 µm in (Panel F2) and (Panel F3). FIG. 3G-H show 3-D reconstructed microCT images of bone defects filled with M-GM+MSCs for kidney capsule transplantation one day (FIG. 3G) or six weeks post-surgery (FIG. 3H). HE and immunofluorescence staining of the explant are shown in the right panel. Scale bars, 1 mm in (FIG. 3H); 200 µm in (Panel H1) and (Panel H2). FIG. 3I shows a schematic drawing showing that M-GM+SCs might provide a niche that recruits endogenous dura mater cells into the regenerated suture, while donor cells also contribute to the self-renewal of surrounding tissues. Bone boundaries are outlined by brown lines.

FIG. 4A-S depict data showing that regenerated sutures show similar gene expression profile and function to natural cranial sutures. FIG. 4A-D show RNAseq analysis of normal sutures (WT), fused sutures (MUT), and the endogenous cells from regenerated sutures (REG). Gene expression profiles are shown with heatmap (FIG. 4A), t-SNE visualization of color-coded regions for the three groups (FIG. 4B), volcano plots indicating the number of differentially expressed genes (FIG. 4C), and gene signatures of Gli1, Prrx1, Axin2, Msx2, and Ostn based on the relative expression levels of WT, MUT, and REG (FIG. 4D). FIG. 4E shows the osteogenic (upper panel, alizarin red staining in inset), chondrogenic (middle panel, whole mount immunostaining and section staining in inset), and adipogenic (lower panel) differentiation ability of cells in the regenerated suture. FIG. 4F-K show the ability of the regenerated suture to repair bone at one day (FIG. 4F-H) or three months post-injury (FIG. 4I-K). MicroCT slices of blank (FIG. 4G, J) and M-GM+SCs (FIG. 4H, K) sides. Red fluorescently labeled cells were from donor mice (Panels K1, K2). Asterisks indicate injuries in parietal bones (FIG. 4G, H, J, K); arrowheads in (FIG. 4H, K) indicate the regenerated sutures. Scale bars, 2 mm in FIG. 4F, I; 1 mm in FIG. 4G, H, J, K; 100 µm in (Panels J1, J2) and (Panels K1, K2). FIG. 4L-S depicts visualization one day (FIG. 4L-N) and three months (FIG. 4O-Q) after transplantation of regenerated sutures or parietal bones without sutures (non-suture transplant) dissected from CAG-EGFP mice. MicroCT slices of non-suture transplant group (FIG. 4M, P) and transplants with sutures (FIG. 4N, Q). In Panel Q1, green fluorescently labeled tissues were from CAG-EGFP mice, while red cells were from donor Gli1-Cre$^{ERT2}$;tdT$^{fl/+}$ mice. Arrowheads indicate the regenerated sutures (FIG. 1, N, O, Q). In FIG. 4R, white dotted lines outline the original size of the transplants, while yellow dotted lines indicate the boundary of the regenerated tissue (R). FIG. 4S shows quantification of the fold change of the transplant surface area from (R). Scale bars, 2 mm in FIG. 4L, O, R; 1 mm in FIG. 4M, N, P, Q; 200 μm in (Panel Q1). Data are mean±s.e.m. (FIG. 4S). **P<0.01, calculated by independent two-tailed Student's t-test.

In FIG. 5A, C, colored dots indicate landmarks of the top calvarium (T-Calvarium) and lateral calvarium (L-Calvarium) shape in all three groups: multiple skull views of normal mice (WT, n=7, blue), Twist1$^{+/-}$ mice with bilateral coronal suture fusion (MUT, n=6, red), and Twist1$^{+/-}$ mice with bilateral coronal suture regeneration (REG, n=5, green). FIG. 5B, D show wireframe deformations representing the shape differences between WT, MUT and REG groups for each region. FIG. 5E, F show total variation between WT, MUT and REG groups was determined by principal component analysis (PCA) for both shape regions. Results of discriminant function analysis (DFA) of three groups for each shape region: top calvarium (Panels E1-E3) and lateral calvarium (Panels F1-F3). Procrustes distance (PD) and P-value (*P<0.05, **P<0.01) were analyzed for every comparison.

FIG. 6A-B show representative intracranial pressure (ICP) traces (FIG. 6A) and quantification (FIG. 6B) of ICP values (WT, n=7; MUT, n=5; REG, n=5 mice). FIG. 6C shows rotarod performance scored as time (seconds) on the rotarod (WT, n=10; MUT, n=12; REG, n=10 mice). FIG. 6D, E show representative animal tracks (FIG. 6D) and preference index (FIG. 6E) of novel object test (WT, n=11; MUT, n=12; REG, n=17 mice). FIG. 6F-H show representative animal tracks (FIG. 6F) and preference indices of sociability (FIG. 6G) and social novelty (FIG. 6H) in the three-chamber test (WT, n=10; MUT, n=12; REG, n=12 mice). FIG. 6I-K show ICP values plotted against preference indices in novel object test (FIG. 6I), sociability (FIG. 6J) and social novelty (FIG. 6K) in the three-chamber test (WT, n=7; MUT, n=6; REG, n=6 mice). Data are mean±s.e.m. FIG. 6B, C, E, G, H. *P<0.05, P<0.01, *P<0.001, NS, not significant calculated by one-way ANOVA (FIG. 6B, E, G) with Tukey post hoc tests and two-tailed unpaired t-test (FIG. 6C).

FIG. 7A show representative magnetic resonance images (MRI) of WT, MUT and REG mouse brains. Hippocampus (Hipp), cortex (Ctx), corpus callosum (Cc) and thalamus (Th) are outlined by yellow or cyan dotted lines. Scale bar, 2 mm. FIG. 7B-F show quantifications of volume of whole brain (FIG. 7B), cortex (FIG. 7C), hippocampus (FIG. 7D), corpus callosum (FIG. 7E) and thalamus (FIG. 7F). (WT, n=5; MUT, n=5; REG, n=5 mice). FIG. 7G-I show representative images of Cux1$^+$ (FIG. 7G), Ctip2$^+$ (FIG. 7H), Tbr1$^+$ (FIG. 7I) cells in somatosensory cortex. Scale bar, 50 μm. FIG.

Figure 7:
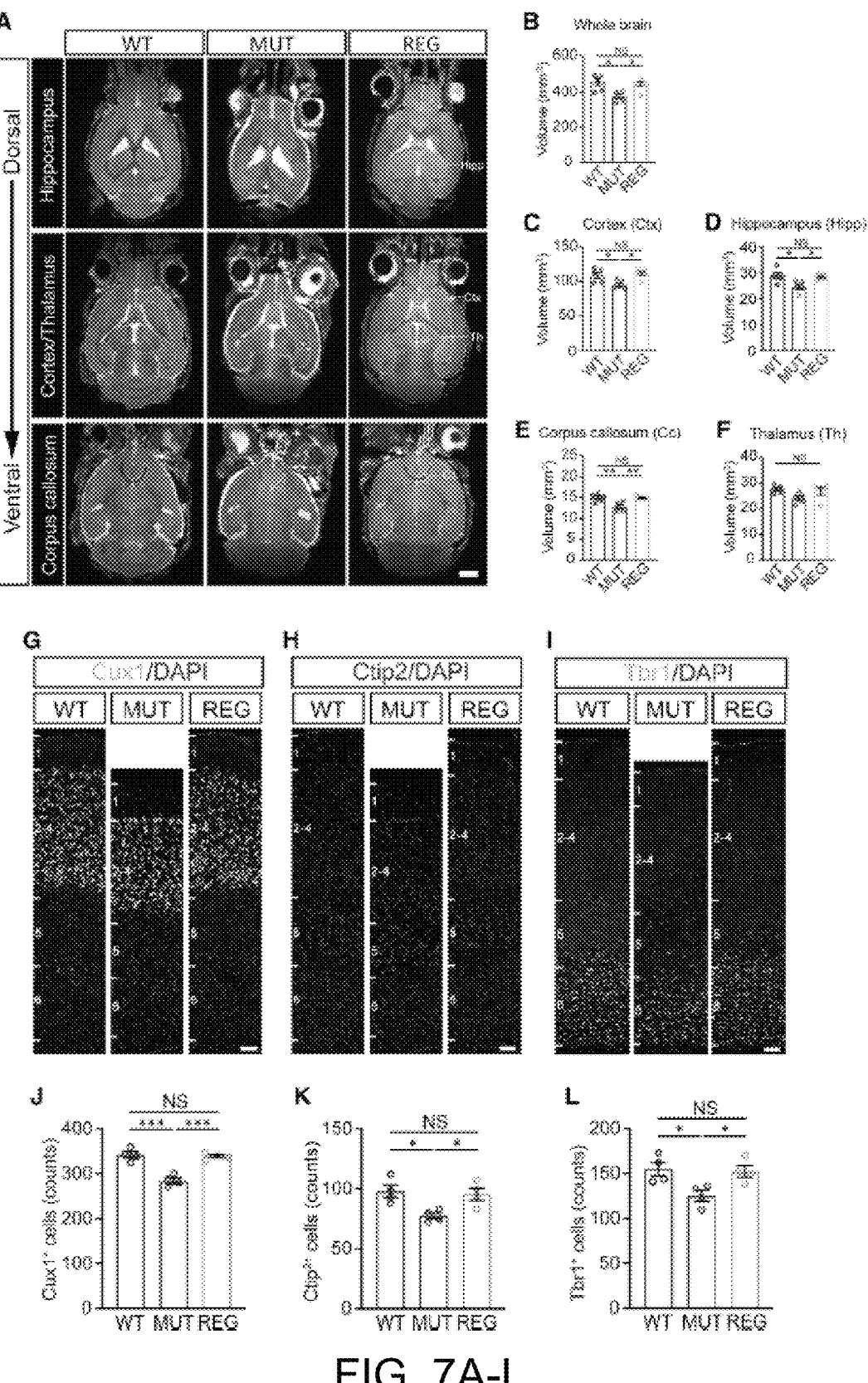
FIG. 7A-L depict data showing that suture regeneration surgery performed at postnatal day 14 restores brain morphology in Twist1$^{+/-}$ mice with craniosynostosis.

7J-L show quantification of Cux1$^+$ (FIG. 7J), Ctip2$^+$ (FIG. 7K), and Tbr1$^+$ (FIG. 7L) cells in somatosensory cortex with 300 μm width (WT, n=4; MUT, n=4; REG, n=4 mice). *P<0.05, P<0.01, *P<0.001, NS, not significant calculated by one-way ANOVA with Tukey post hoc tests.

Figure 8:
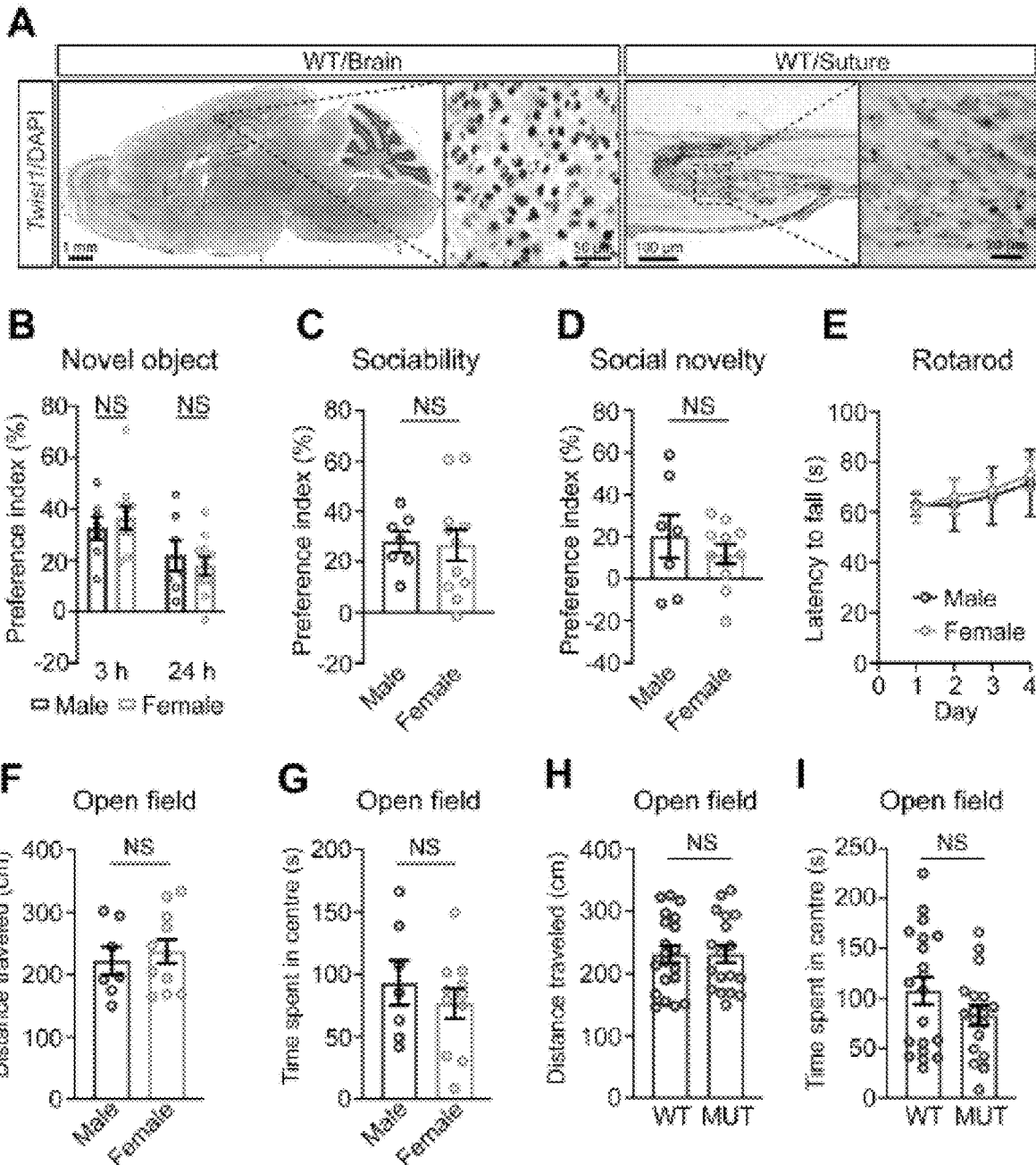

FIG. 8A-I depicts analysis of Twist1 expression, cognitive and motor learning-related behavior in adult mice. Twist1 is expressed in the cranial suture mesenchyme but is absent from the brain in adult mice. Cognitive- and motor learning-related behavioral deficits of Twist1$^{+/-}$ mice are not sex-biased. FIG. 8A: In situ hybridization of Twist1 gene transcripts of WT brain (left) and coronal suture (right) of one-month-old C57BL/6J mice. Red signal indicates positive Twist1 expression. FIG. 8B-D: Preference indices for novel object (FIG. 8B), sociability (FIG. 8C) and social novelty (FIG. 8D) during the three-chamber test. FIG. 8E: Rotarod performance scored as time on the rotarod. FIG. 8F, G: Total traveled distance (FIG. 8F) and time spent in the center area (FIG. 8G) during the open field test (Male, n=7; Female, n=11 mice). FIG. 8H, I: Total traveled distance (FIG. 8H) and time spent in the center area (FIG. 8I) during the open field test (WT, n=20; Mut, n=20 mice). Data are mean±s.e.m.*P<0.05, ****P<0.0001, NS, not significant calculated by two-tailed unpaired t-test.

Figure 9:
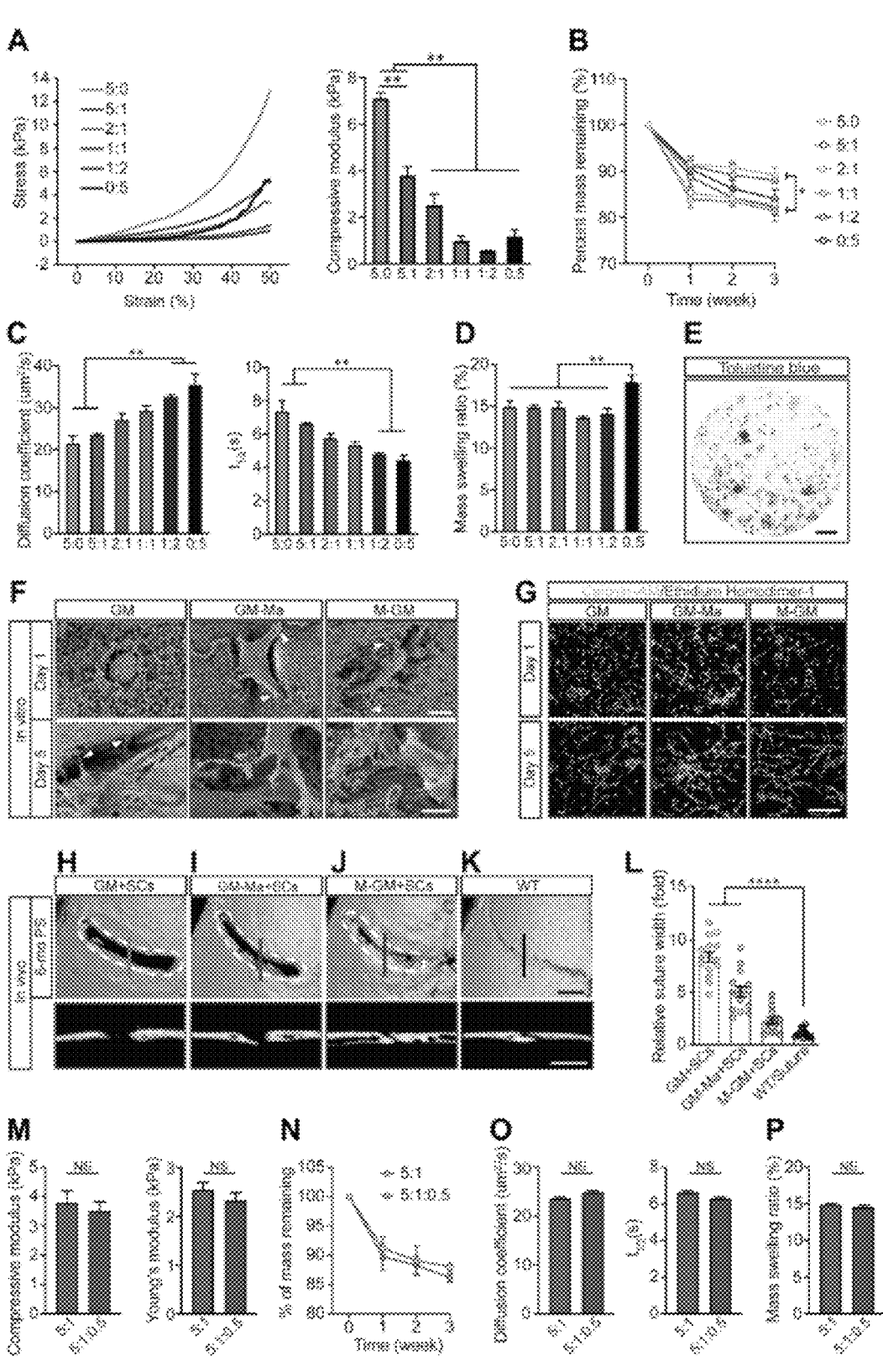

FIG. 9A-P depicts data showing that GelMA:Matrigel: Col-I at a ratio of 10:2:1 (M-GM) provides a suitable material for suture regeneration. FIG. 9A-D: Material properties of (1) pure GelMA (5:0), (2) GelMA:Matrigel at a ratio of 5:1, (3) GelMA:Matrigel at 2:1, (4) GelMA:Matrigel at 1:1, (5) GelMA:Matrigel at 1:2, and (6) pure Matrigel, including compressive modulus (FIG. 9A), degradation rate (FIG. 9B), diffusional permeability (FIG. 9C), and mass swelling ratio (FIG. 9D). Data are expressed as mean±s.e.m.,*P<0.05, P<0.01, not significant calculated by one-way ANOVA with Tukey post hoc test. FIG. 9E: Toluidine blue staining for colony-forming assay of Gli1$^+$ cells cultured 7 days in vitro. Scale bar, 2 mm. FIG. 9F: Morphology of cells in pure GelMA (GM) (left), GelMA: Matrigel at 5:1 ratio (GM-Ma) (middle), and M-GM (right) assessed by SEM 1 and 5 days after culturing. Arrowheads indicate pseudopodia. Scale bar, 10 μm in upper panel; 5 μm in lower panel. FIG. 9G: Cellular viability detected with live/dead staining kit after 3-D culturing for 1 and 5 days in GM (left), GM-Ma (middle), and M-GM (right). Immunocytochemistry with Calcein-AM (green) for living cells, Ethidium Homodimer-1 (red) for dead cells. Scale bar, 200 μm. FIG. 9H-K: Representative microCT images (upper panel, 3-D reconstruction; lower panel, slice) of GM plus suture MSCs (GM+SCs; FIG. 9H), GM-Ma plus suture MSCs (GM-Ma+SCs; FIG. 9I), M-GM plus suture MSCs (M-GM+SCs; FIG. 9J) at six months post-surgery, and the coronal suture of seven-month-old control (FIG. 9K). Dotted lines (white) outline the original surgical defects. Scale bar, 200 μm. FIG. 9L: Quantification of suture width (FIG. 9H-K). Data are expressed as mean±s.e.m. (FIG. 9L). **P<0.0001, calculated by one-way ANOVA with Tukey post hoc tests. FIG. 9M-P: Comparison of material properties of GM-Ma (5:1) and M-GM (5:1:0.5): compressive modulus/tensile strength (FIG. 9M), degradation rate (FIG. 9N), diffusional permeability (FIG. 9O), and mass swelling ratio (FIG. 9P). Data are expressed as mean±s.e.m., not significant calculated by two-tailed unpaired t-test.

Figure 10:
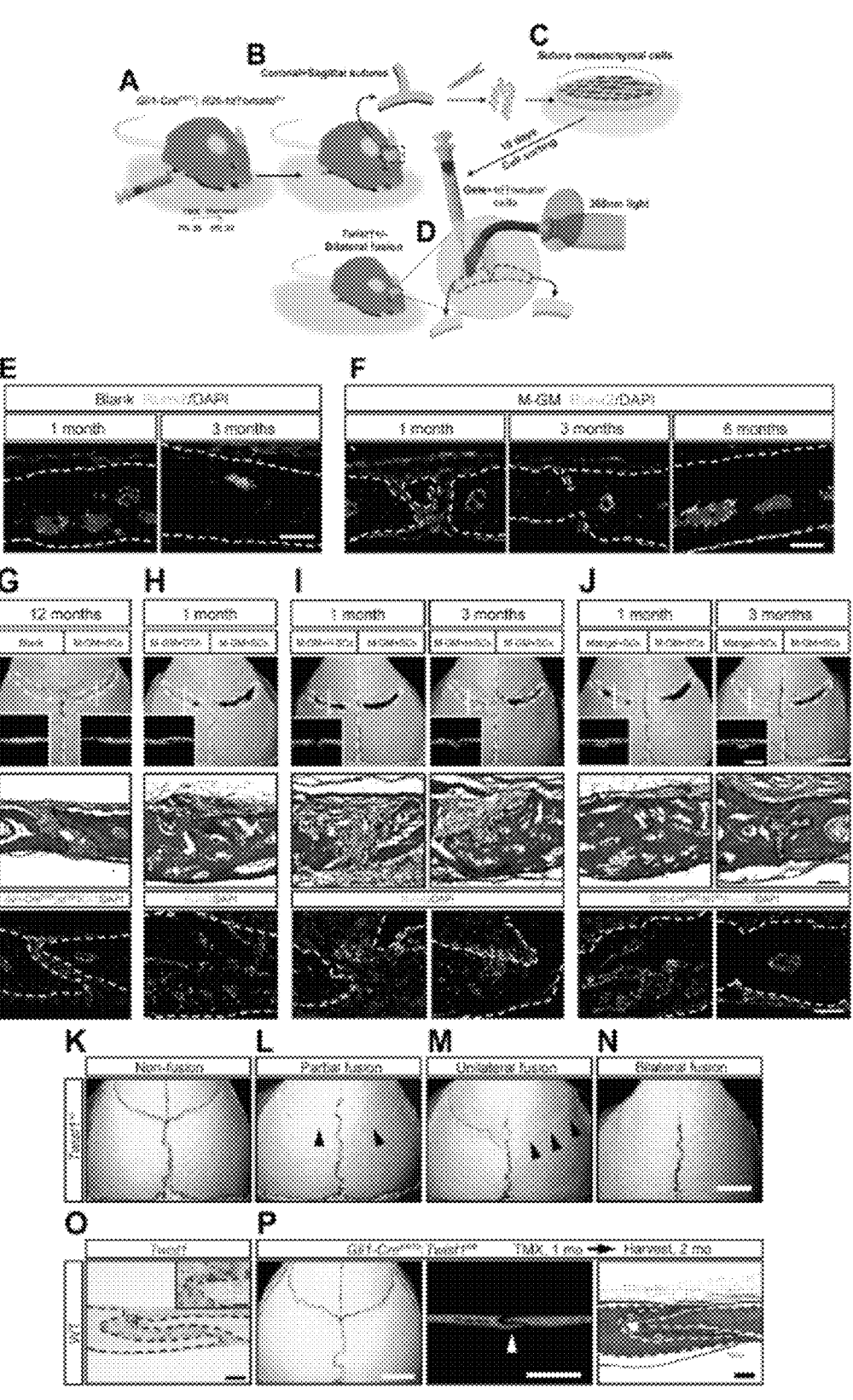

FIG. 10A-D depict a schematic of suture regeneration. FIG. 10A: One-month-old Gli1-Cre$^{ERT2}$; ROSA26$^{LoxP-STOP-LoxP-tdTomato}$ mice after two days of injection with tamoxifen. FIG. 10B: Coronal and sagittal sutures were excised from the mice and minced into tiny pieces for cell culture. FIG. 10C: After 10 days of expansion in vitro, tdTomato$^+$ cells were acquired from suture mesenchymal cells by cell sorting. FIG. 10D: After generating defects in the region of the fused sutures, cells mixed with carrier gel biomaterial was placed in the defects and gel was cured with UV light. The wound was then closed carefully.

FIG. 10E-J depict data showing that Gli1+ cells and M-GM are required for long-term suture patency. FIG. 10E-F: Immunofluorescence staining for blank (FIG. 10E, one and three months post-surgery), and M-GM (FIG. 10F, one, three and six months post-surgery) groups. Scale bar, 100 μm. FIG. 10G-J: MicroCT imaging (upper panel), HE (middle panel) and immunofluorescence (lower panel) staining of M-GM+SCs one year post-surgery (FIG. 10G), M-GM plus suture mesenchymal cells from one-month-old Gli1-Cre$^{ERT2}$; ROSA26$^{LoxP-STOP-LoxP-eGFP-DTA}$ mice one month post-surgery (M-GM+DTA cells; 1M PS) (FIG. 10H), M-GM plus heat-activated suture MSCs at one month (M-GM+H-SCs; 1M PS) or three months (M-GM+H-SCs; 3M PS) post-surgery (FIG. 10I), matrigel plus Gli1$^+$ MSCs at one month (MG+SCs; 1M PS) or three months (MG+SCs; 3M PS) post-surgery (FIG. 10J).Red fluorescently labeled cells were from one-month-old donor Gli1-Cre$^{ERT2}$;tdT$^{fl/+}$ mice (FIG. 10G, J). Insets show CT slices of different regions. Dotted lines in 3-D reconstructed images outline the initial defects. All other white dotted lines represent boundaries of bones. Scale bars, 1 mm in insets in (FIG. 10G-J); 2 mm in upper panel of (FIG. 10G-J); 100 μm elsewhere.

FIG. 10K-N depicts data showing that Twist1$^{+/-}$ mice show coronal suture fusion with variations. FIG. 10K-N: 3-D reconstructed microCT images of calvaria of one-month-old Twist1$^{+/-}$ mice with different coronal suture phenotypes: non-fusion (FIG. 10K), partial fusion (FIG. 10L), unilateral fusion (FIG. 10M), and bilateral fusion (FIG. 10N); arrows in (FIG. 10L, M) point to fused sutures. Scale bar, 2 mm.

FIG. 10O-P depict data showing Twist1 in coronal suture of adult mice. (FIG. 10O) RNAscope of Twist1 (red) in the coronal suture of one-month-old wild type mouse. Scale bar, 100 μm. FIG. 10P: 3-D reconstruction (left), microCT slice images (middle), and HE staining (right) of two-month-old Gli1-Cre$^{ERT2}$;Twist1$^{fl/fl}$ mice after three days of tamoxifen injection at one month. The arrowhead indicates the coronal suture. White dotted lines indicate boundaries of bones. Scale bars, 2 mm in left, 1 mm in middle and 100 μm in right panel.

Figure 11:
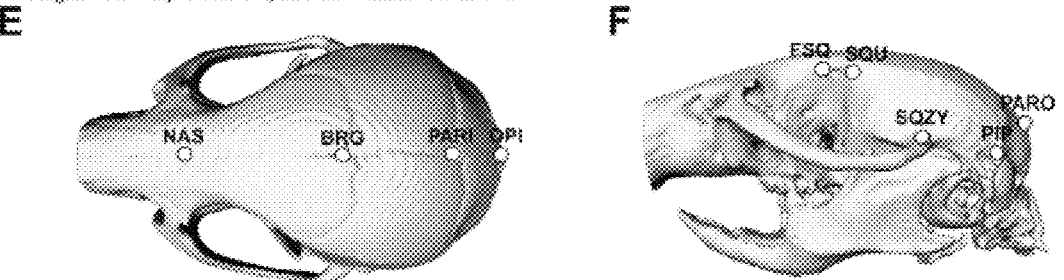

FIG. 11A-C depict Wnt signaling analysis in craniosynostosis and suture regeneration. Wnt signaling is upregulated in craniosynostosis and regenerating suture restores the normal expression of Wnt-related genes. FIG. 11A: Western blot analyses of Runx2 and OPN expression in suture mesenchymal cells after Wnt activator (Wnt agonist 1) or GSK3 inhibitor (activator of Wnt signaling, LY2090314) treatment for one or two weeks. FIG. 11B: Quantification of Runx2 and OPN expression after Wnt agonist 1/LY2090314 or vehicle treatment. Data are expressed as mean±s.e.m., *P<0.05, P<0.01, *P<0.001, **P<0.0001, not significant calculated by two-tailed unpaired t-test. FIG. 11**C: Signatures of Wnt-related genes based on the relative expression levels of WT, MUT, and endogenous cells from REG.

FIG. 11D-F depict landmarks for analyzing head shape. FIG. 11D: Table of landmark descriptions for analyzing head shape. FIG. 11E-F: Superior (FIG. 11E) and lateral views (FIG. 11F) of landmark locations.

Figure 12:
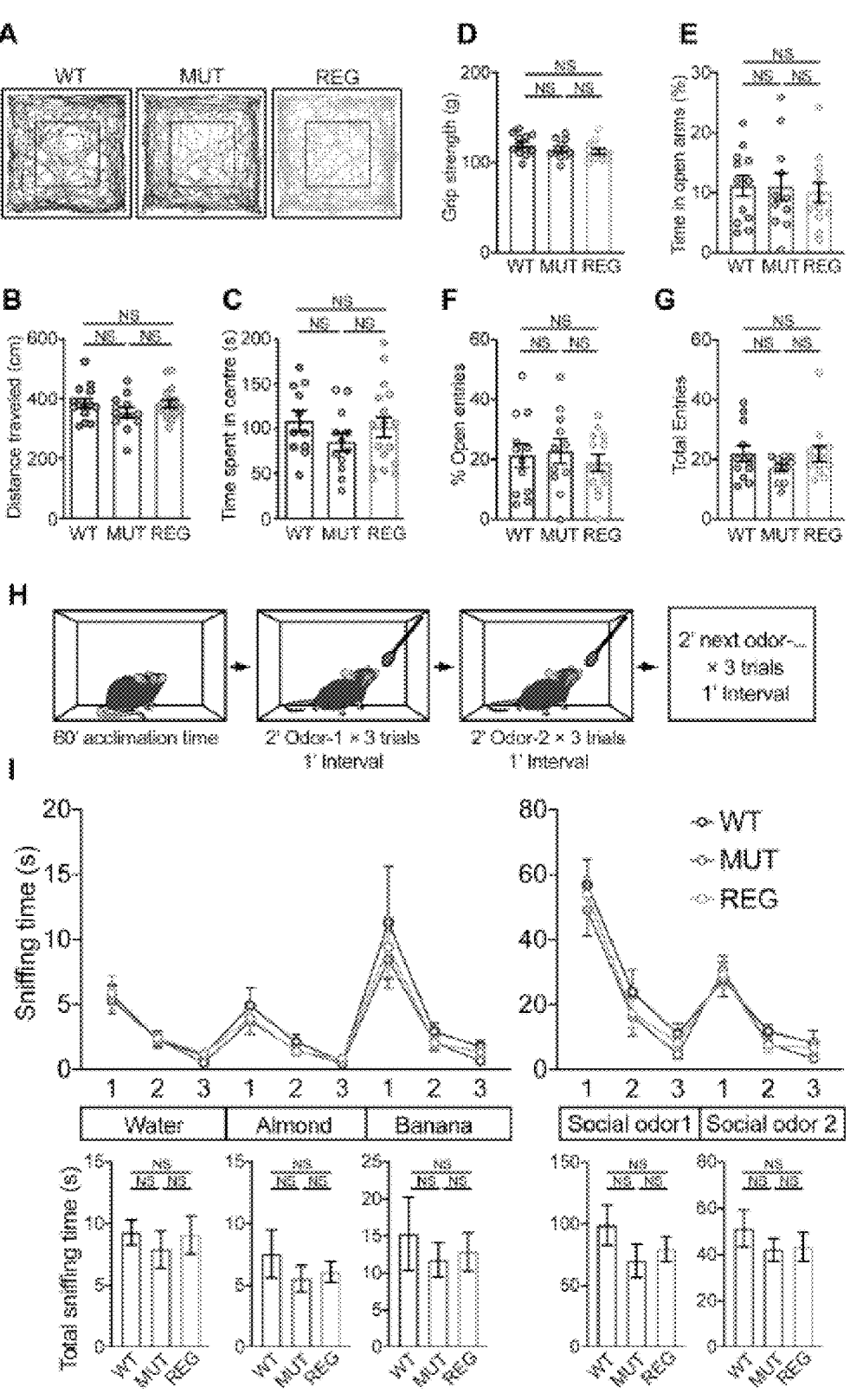

FIG. 12A-I depict analyses of locomotion, grip strength, olfactory function, and anxiety-related behaviors. FIG. 12A:

Representative tracks of the open field test. Total traveled distance (FIG. 12B) and time spent in the center area (FIG. 12C) during the open field test (WT, n=11; MUT, n=12; REG, n=17 mice). FIG. 12D: Comparison of grip strength (WT, n=12; MUT, n=11; REG, n=13 mice).Rate of time spent in open arms (FIG. 12E), number of open entries (FIG. 12F) and total entries (FIG. 12G) during elevated plus maze test (WT, n=12; MUT, n=11; REG, n=13 mice).FIG. 12H: Schematic of odor discrimination/habituation test. FIG. 12I: Time spent sniffing non-social odors (upper left panel) and social odors (upper right panel) during odor discrimination and habituation test. The lower panel shows the total sniffing time per olfactory cue (WT, n=12; MUT, n=11; REG, n=13 mice). Data are mean±s.e.m. (FIG. 12B, C, D, E, F, G, I). P<0.01, *P<0.001, ****P<0.0001, NS, not significant calculated by one-way ANOVA with Tukey's test.

Figure 13:
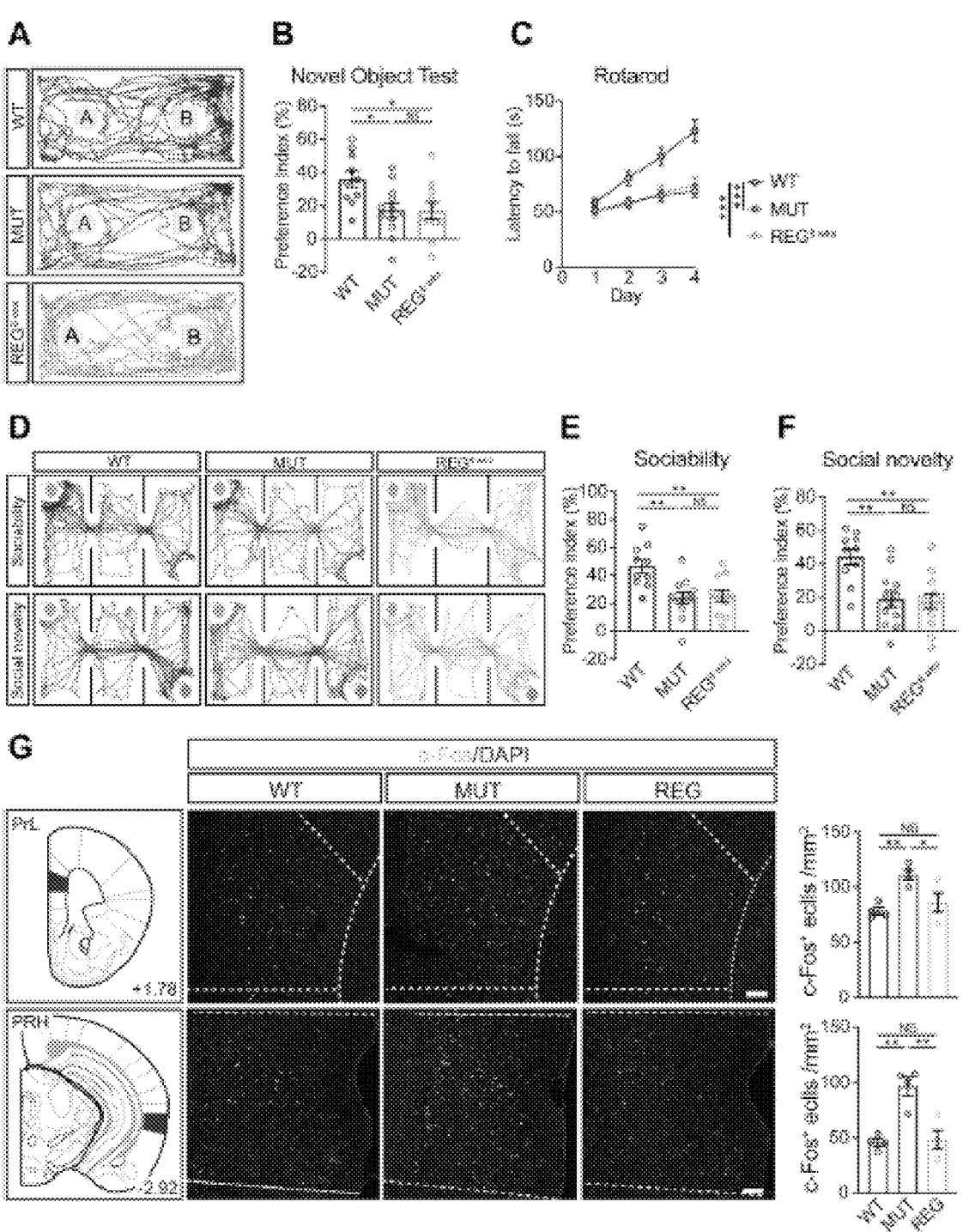

FIG. 13A-F depict data showing that rescue of cognitive and motor learning defects of Twist1$^{+/-}$ mice with craniosynostosis is age dependent. Suture regeneration surgery performed at two months of age fails to rescue cognitive and motor learning defects of Twist1$^{+/-}$ mice with craniosynostosis. Representative animal tracks in novel object test (FIG. 13A) and three chamber test (FIG. 13D). Preferential indices in novel object test (FIG. 13B), sociability (FIG. 13E) and social novelty (FIG. 13F) in three-chamber test. FIG. 13C: Rotarod performance scored as time (seconds) on the rotarod. WT, wild-type mice, n=10; MUT, Twist1$^{+/-}$ mice with bilateral suture fusion, n=12; REG$^{8~wks}$, Twist1$^{+/-}$ mice with suture regeneration surgery performed at two months of age, n=13. Data are mean±s.e.m. (FIG. 13B, C, E, F). *P<0.05, P<0.01, *P<0.001, **P<0.0001, NS, not significant calculated by one-way ANOVA (FIG. 13B, E, F) with Tukey post hoc tests and two-tailed unpaired t-test (FIG. 13**C).

FIG. 13G depicts c-Fos expression analysis. c-Fos is activated at an increased level in the prelimbic and perirhinal cortex in Twist1$^{+/-}$ mice, and could be reduced by suture regeneration. Left panel, schematics of brain coronal sections. Prelimbic cortex (PrL), and perirhinal cortex (PRH) are highlighted with red. The number on the right bottom corner of each panel indicates the distance (mm) from bregma. Middle panel, representative images of c-Fos expression in PrL (top panel) and PRH (bottom panel). Dotted lines indicate the boundaries of PrL, and PRH. Scale bar, 50 μm. Right panel, quantification of c-Fos expression in PrL (top panel), and PRH (bottom panel) (WT, n=4; MUT, n=4; REG, n=4 mice). *P<0.05, P<0.01, *P<0.001, NS, not significant calculated by one-way ANOVA with Tukey's post hoc test.

Figure 14:
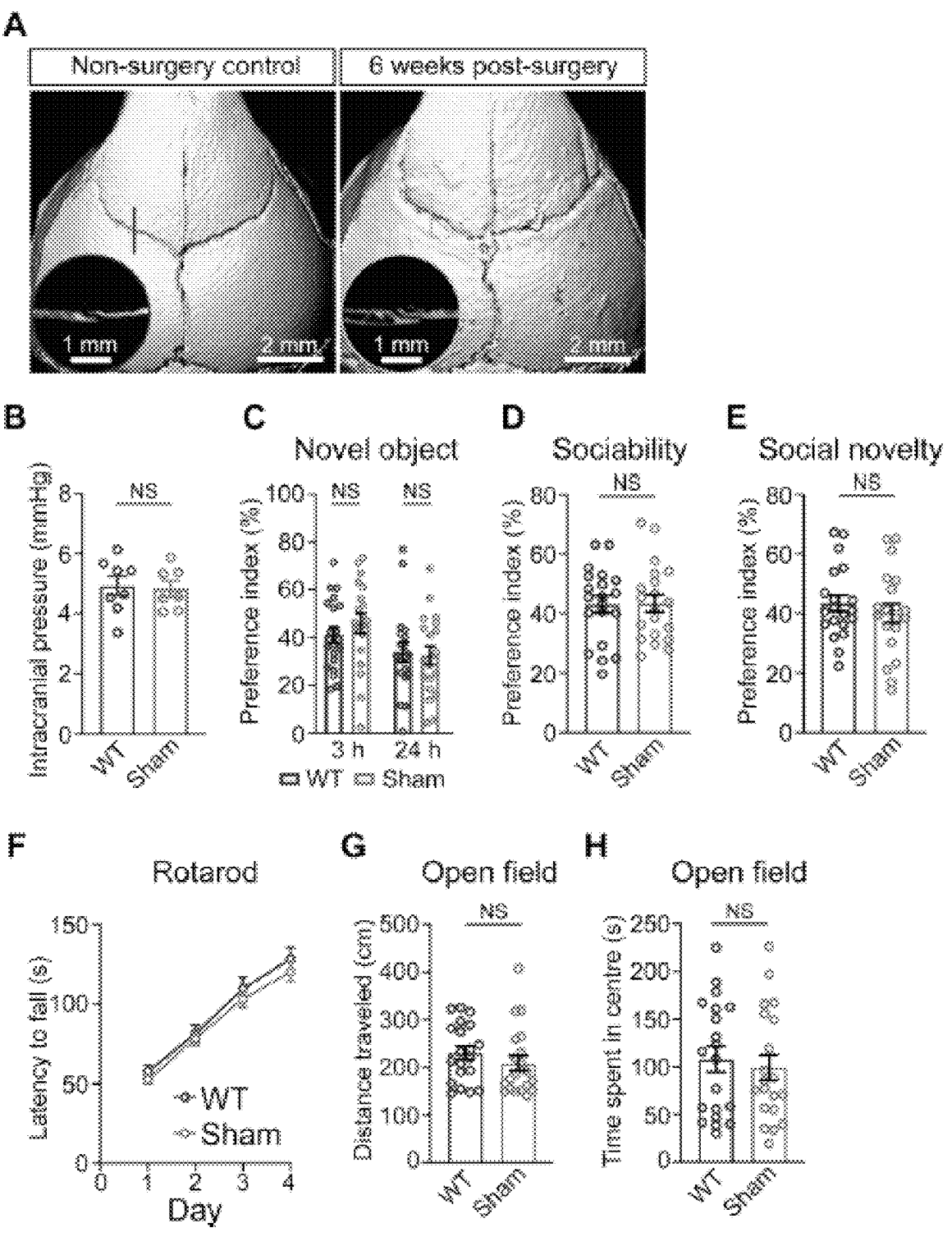

FIG. 14A-H depicts data showing that calvarial injury surgery does not cause elevated ICP or behavioral abnormalities. FIG. 14A: MicroCT images (3-D reconstruction and slice) for wild type mice at two-weeks-old age before or six weeks post-surgery. Scale bars, 1 mm in inset; 2 mm in (FIG. 14A). FIG. 14B: Quantification of ICP values (WT, n=8; Sham, n=7 mice). Preference indices of novel object test (FIG. 14C), sociability (FIG. 14D) and social novelty (FIG. 14E) during the three-chamber test. FIG. 14F: Rotarod performance scored as time (seconds) on the rotarod (WT, n=20; Sham, n=18 mice). Total traveled distance (FIG. 14G) and time (seconds) spent in the center area (FIG. 14H) during the open field test (WT, n=20; Sham, n=20 mice). Data are mean±s.e.m. (B-H). NS, not significant calculated by two-tailed unpaired t-test.

Figure 15:
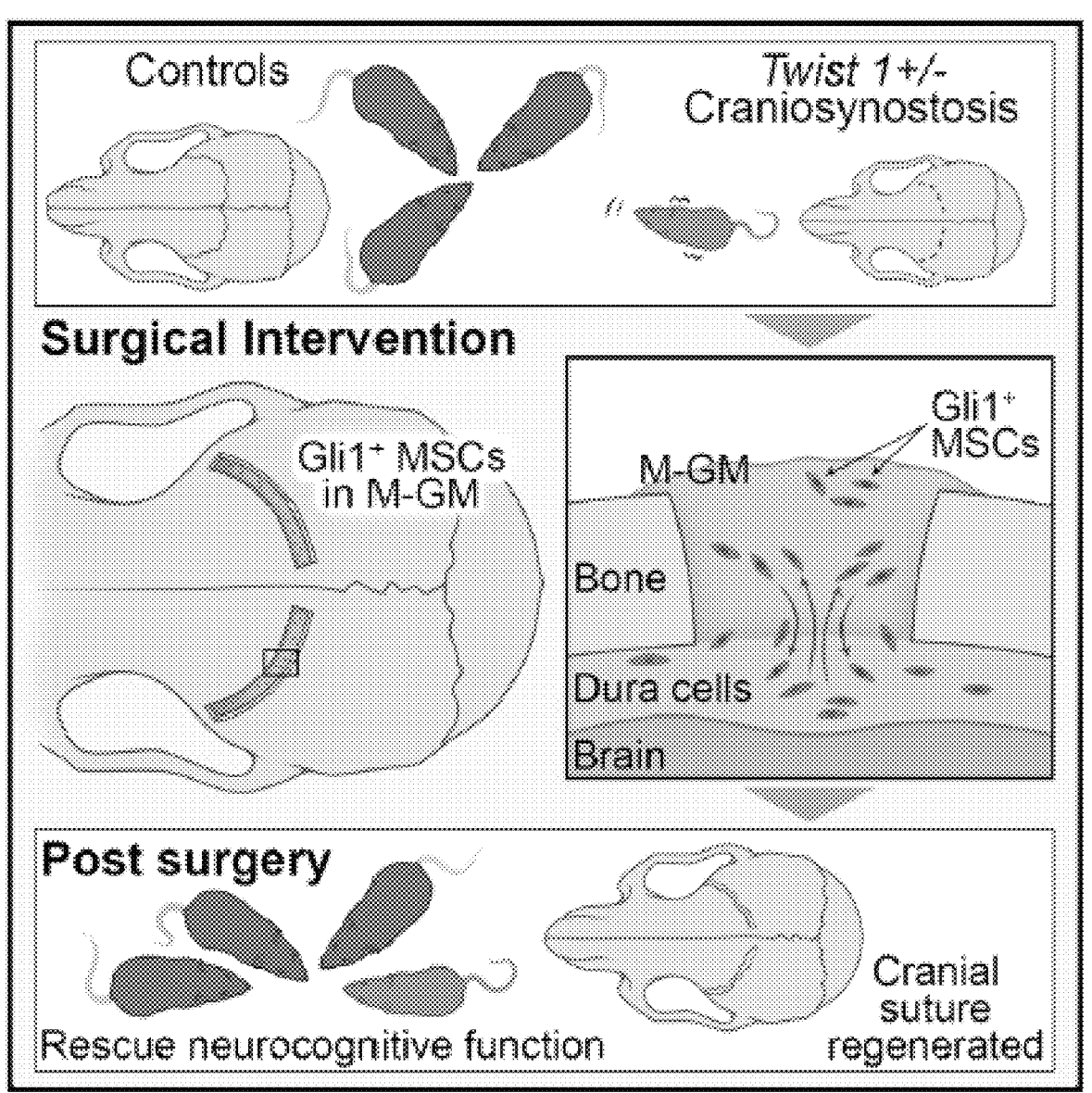

FIG. 15 depicts a schematic for treating craniosynostosis with the compositions described herein.

DETAILED DESCRIPTION

This disclosure relates to compositions and methods that may be used regeneration of cranial sutures and treatment of craniosynostosis, which can help reverse increased intracranial pressure and skull and neurocognitive abnormalities.

In this disclosure, the composition, which may be used for regeneration of cranial sutures and treatment of craniosynostosis, may include methacrylated gelatin (GelMA), extracellular matrix, and collagen I. This composition may further include Gli1+ mesenchymal stem cells.

Mesenchymal stem cells (MSCs) can self-renew and differentiate into an array of different cell types for tissue regeneration, and have been used to regenerate calvarial bone. $Gli1^+$ cells are an indispensable MSC source within the cranial sutures. They support craniofacial bone turnover, repair and regeneration in adult mice. Importantly, there is premature loss of $Gli1^+$ cells prior to coronal suture fusion in $Twist1^{+/-}$ mice. This suggests that restoring MSCs represents a potential therapeutic approach for cranial suture regeneration in craniosynostosis. However, this approach presents substantial technical challenges, as the method of MSC delivery and the biomaterial(s) used in the defect area are crucial. It is not well understood how MSCs may participate in the cranial suture regeneration process or what are the ideal biomaterials to support them.

As shown herein, premature fusion of the coronal suture led to increased ICP and neurocognitive abnormalities in $Twist1^{+/-}$ mice, recapitulating symptoms of Saethre-Chotzen syndrome in humans. Using this clinically relevant mouse model, it was demonstrated that Gli1+MSCs combined with modified methacrylated gelatin (GelMA) can support coronal suture regeneration. Endogenous MSCs migrated to the regenerated suture area to sustain its function in calvarial tissue homeostasis and repair. Significantly, suture regeneration reduced ICP, partially alleviated calvarial deformity, and improved neurocognitive function. As TWIST1 haploinsufficiency is associated with craniosynostosis in patients with Saethre-Chotzen syndrome, this offers a unique approach for improving the quality of life for craniosynostosis patients.

By combining MSCs with biomaterials and establishing a mouse model of neurocognitive defects associated with craniosynostosis, it was shown that $Gli1^+$ MSC-based cranial suture regeneration restores not only skull dysmorphology, but also neurocognitive dysfunctions in the $Twist1^{+/-}$ mouse model of craniosynostosis. These findings represent a research paradigm shift and provide a MSC-based therapeutic strategy for treating craniosynostosis with potential beneficial impacts on clinical practice.

Mutant animal models have been instrumental in elucidating the molecular and cellular etiology of craniosynostosis. Many of these models phenocopy the synostoses seen in patients with the same genetic mutation, making them highly valuable. However, nearly all studies have focused exclusively on cranial suture defects; analysis of the ICP and neurocognitive functions of these models has been lacking. Here, $Twist1^{+/-}$ mice have been established to model neuroanatomic and cognitive dysfunctions in craniosynostosis patients. Disclosed herein is an effective treatment in which Gli1+MSCs and modified GelMA support cranial suture regeneration and correct skull dysmorphology in $Twist1^{+/-}$ mice with craniosynostosis.

Surgical correction of craniosynostosis is routinely performed within the first year of life. Whole-vault cranioplasty and endoscopic synostectomy followed by skull molding helmet therapy are the most common treatments currently. However, these procedures are invasive and are associated with resynostosis and other complications. An improved treatment option is needed to ensure long-term quality of life for these young patients. The successful MSC-based suture regeneration provided herein depends on a uniquely modified GelMA (M-GM) scaffold that is biocompatible with $Gli1^+$ MSCs, biodegradable, and provides excellent support for suture regeneration. This therapeutic strategy regenerates cranial sutures that remain patent for at least one year and continue to function similarly to a natural cranial suture in injury repair and maintaining tissue homeostasis. These results suggest that MSCs implanted with M-GM present a less invasive and sustainable biological solution for patients with craniosynostosis.

The evidence herein provide cellular and molecular insights into the cranial suture regeneration and maintenance processes. The importance and inter-dependence of exogenously implanted $Gli1^+$ MSCs and endogenous MSCs derived from the dura mater in cranial suture regeneration in $Twist1^{+/-}$ mice was shown. This is consistent with the crucial role of multipotent progenitors within the dura mater in calvarial tissue homeostasis. MSC grafts can recruit endogenous stem cells to regeneration sites, likely facilitated by Wnt3a, PDGF, and VEGF. At the molecular level, haploinsufficiency of Twist1 leads to compromised Axin2 and elevated Wnt signaling. Implantation of exogenous MSCs restored Wnt signaling to a level comparable to control samples, preventing resynostosis. Furthermore, it was shown that postnatal functions of Twist1 are not essential, as loss of Twist in $Gli1^+$ MSCs does not lead to craniosynostosis in adult mice. This result also partially explains how implanted MSCs, along with recruited endogenous $Gli1^+$ MSCs, can regenerate a patent cranial suture despite haploinsufficiency of Twist1. Collectively, this suggests that implanted MSCs establish a conducive niche into which there is dynamic recruitment and integration of endogenous MSCs to support the regeneration of a functional and sustainable cranial suture.

Restoration of suture patency not only rescues skull deformity but also normalizes ICP and restores neurocognitive function. Patients with craniosynostosis often have learning disabilities. Non-syndromic craniosynostosis affecting different cranial sutures may have differential effects on neurocognitive function. The suture regeneration approach provided herein rescued several behavioral abnormalities in $Twist1^{+/-}$ mice, including deficits in novel object recognition, sociability, and social novelty. This suggests that elevated ICP causes, at least in part, neurocognitive dysfunctions which are rescued by suture regeneration in $Twist1^{+/-}$ mice with craniosynostosis. The MRI and histological studies herein indicate that changes in neural numbers and brain volume contribute to neurocognitive dysfunctions in $Twist1^{+/-}$ mice, and these changes are restored following suture regeneration. This provides important insights into the mechanisms underlying improvement of neurocognitive functions by suture regeneration. Twist1 is not expressed in the adult mouse brain and $Twist1^{+/-}$ mice without craniosynostosis have normal ICP and neurocognitive function, suggesting that Twist1 does not have a direct role in regulating the development and function of brain structures. In humans, however, TWIST1 is expressed in the cerebral cortex during fetal development and upper layer excitatory neurons in adults.

In summary, it was demonstrated that MSCs combined with M-GM can regenerate a cranial suture, restore normal ICP, and rescue neurocognitive function in a highly clinically relevant craniosynostosis model. This cranial suture regeneration approach offers an effective and less invasive treatment option for craniosynostosis, bringing new hope for patients who suffer from this devastating disease.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

In this disclosure, Gli1+ mesenchymal stem cells may be suspended in the composition at a density, expressed in a number of cells per milliliter (mL) of the composition, in a range of $0.1 \times 10^7$ cells/mL to $50 \times 10^7$ cells/mL, or in a range of $1 \times 10^7$ cells/mL to $20 \times 10^7$ cells/mL, or in a range of $2 \times 10^7$ cells/mL to $10 \times 10^7$ cells/mL, or in a range of $3 \times 10^7$ cells/mL to $7 \times 10^7$ cells/mL. The said density may also be about $5 \times 10^7$ cells/mL.

In this disclosure, GelMA in the composition may be at a concentration, expressed in percent weight (w) of GelMa per volume (v) of the composition, in a range of 1% w/v to 10% w/v, or in a range of 2% w/v to 6% w/v, or in a range of 3% w/v to 5% w/v, or in a range of 3.5% w/v to 4.2% w/v, or in a range of 3.7% w/v to 4.0% w/v. The said concentration may also be in a range of 3.8% w/v to 3.9% w/v.

In this disclosure, extracellular matrixin the composition may be at a concentration, expressed in percent volume (v) of extracellular matrix per volume (v) of the composition, in a range of 1% v/v to 30% v/v, or in a range of 10% v/v to 20% v/v, or in a range of 13% v/v to 17% v/v, or in a range of 14% v/v to 16% v/v. The said concentration may also be about 15% v/v.

In this disclosure, collagen I in the composition may be at a concentration, expressed in a microgram (μg) of collagen I in per milliliter (mL) of the composition, in a range of 100 μg/mL to 400 μg/mL, or in a range of 200 μg/mL to 300 μg/mL, or in a range of 210 μg/mL to 260 μg/mL, or in a range of 220 μg/mL to 250 μg/mL.

The disclosure is generally disclosed herein using affirmative language to describe the numerous embodiments. The disclosure also includes embodiments in which subject matter is excluded, in full or in part, such as substances or materials, method steps and conditions, protocols, or procedures.

EXAMPLES

Some aspects of the embodiments discussed herein are disclosed in further detail in the following examples, which are not in any way intended to limit the scope of the present disclosure. Those in the art will appreciate that many other embodiments also fall within the scope of the disclosure, as it is described herein and in the claims.

Example 1. Twist1$^{+/-}$ Mice with Craniosynostosis Exhibit Increased ICP and Neurocognitive Abnormalities To investigate whether craniosynostosis can lead to intracranial hypertension and neurocognitive behavioral abnormalities in Twist1$^{+/-}$ mice, as reported in humans, we first measured the ICP in Twist1$^{+/-}$ mice with craniosynostosis (referred to as MUT) and wildtype (WT) littermate controls (FIG. 1A) at two months of age. Twist1$^{+/-}$ mice had significantly increased ICP compared to WT (FIG. 1B, 1C). Then we conducted a battery of cognitive behavioral tests. Data from both male and female mice were combined for the statistical analyses as no sex-biased preference was observed (FIG. 8B-8G). In open field and elevated plus maze tests, Twist1$^{+/-}$ mice spent comparable time in the center area of the open field arena (FIG. 8I) and similar time and entries in the open arms of the elevated plus maze as their WT littermates (FIG. 12E-12G), which indicated that Twist1$^{+/-}$ mice did not have unusual levels of anxiety.

In the novel object test (FIG. 1F), the preference for a novel object was significantly impaired in Twist1$^{+/-}$ mice with craniosynostosis compared to WT controls (FIG. 1G, 1H), suggesting a hippocampus-dependent spatial memory deficit. To assess social cognition, a three-chamber test was performed (FIG. 1I). The preferences for investigating the mouse versus empty cage and novel versus familiar mouse were significantly decreased in Twist1$^{+/-}$ mice with craniosynostosis (FIG. 1J, 1K), indicating impaired sociability and social novelty. To exclude the possibility that the impaired cognitive functions in Twist1$^{+/-}$ mice with craniosynostosis may be caused by olfactory dysfunctions, we performed an odor discrimination/habituation test (FIG. 12H) and found that Twist1$^{+/-}$ mice with craniosynostosis could distinguish among and habituate to nonsocial and social odors to the same degree as their WT littermates, which suggested they had normal olfaction (FIG. 12I). We examined motor learning ability using a rotarod test (FIG. 1D). WT control mice exhibited an increased latency to falling off the accelerating rotarod (4-40 rpm in 5 min) over four consecutive days, indicating active learning (FIG. 1E). In contrast, Twist1$^{+/-}$ mice with craniosynostosis did not exhibit obvious improvement, suggesting a significant motor learning deficit. We next measured motor functions and did not find an obvious difference in grip strength (FIG. 12D) or total distance traveled in the open field arena (FIG. 8H), which suggested normal motor strength of Twist1+/mice with suture fusion. Together, these results suggested that Twist1$^{+/-}$ mice have neurocognitive dysfunctions. We suspected that these deficits were mediated by their elevated ICP, as Twist1 expression is not detected in the brain in adult mice, so its haploinsufficiency is unlikely to have a direct effect on neurocognition (FIG. 8A).

Example 2. Modified GelMA Provides a Favorable Environment for Suture MSCs

To optimize the formulation of a scaffold for Gli1+ cells to support the regeneration of a new coronal suture in Twist1$^{+/-}$ mice with craniosynostosis, we compared several different biomaterials. Briefly, we tested different formulations of methacrylated gelatin (GelMA) modified with Matrigel and collagen I (COL-I). GelMA has excellent biocompatibility and is easy to use in a surgical setting as it conforms to defects and can be light-cured in seconds. The addition of Matrigel promotes the spread of cells inside the scaffold, while collagen I helps form a suitable suture space as shown below.

Before settling on the final formulation, we tested some variations: (1) pure GelMA, (2) GelMA:Matrigel at a ratio of 5:1, (3) GelMA:Matrigel at 2:1, (4) GelMA:Matrigel at 1:1, (5) GelMA:Matrigel at 1:2, and (6) pure Matrigel. Pure GelMA and GelMA:Matrigel (5:1) had a higher compressive modulus than the other materials (FIG. 9A), which would better maintain the space between bones after surgery for suture regeneration. The tensile strength was also tested, and there was no significant difference between pure GelMA and GelMA:Matrigel (5:1), while the remaining four groups were too soft to be measured.

After being soaked/rinsed for three weeks, the remaining mass of pure GelMA and GelMA:Matrigel (5:1) remained higher than those of other groups (i.e. they had the lowest degradation rate), which would also help prevent suture refusion after surgery (FIG. 9B). Diffusional permeability testing showed that the pure GelMA and GelMA:Matrigel (5:1) had the lowest diffusional ability, which may help to block the intrusion of cytokines, such as angiogenesis factors that could promote bone formation and suture refusion (FIG. 9C). Using pure Matrigel, which had the highest diffusional permeability, suture refusion occurred in as soon as one month (FIG. 10J). The swelling ratio showed similar results to the diffusional permeability testing, which suggested that a solution like blood could more easily get into the pure Matrigel and promote bone formation, while there was no significant difference between the other five groups (FIG. 9D).

Taking all these properties into account, we concluded that pure GelMA and GelMA:Matrigel at a 5:1 ratio have the most favorable properties for suture regeneration. It is important to note that Matrigel, a mouse tumor matrix preparation, may be limited in its application for patient use.

We compared GelMA:Matrigel:COL-I at a ratio of 10:2:1 (M-GM) to pure GelMA (GM) and GelMA:Matrigel at a ratio of 5:1 (GM-Ma). Both SEM (FIG. 9F) and cellular viability staining (FIG. 9G) showed that cells could spread more easily in GM-Ma and M-GM in three-dimensional culture. After six months, M-GM with MSCs formed a regenerated suture more similar to a natural one (FIG. 9H-9L), which suggested COL-I could attract osteo-related cells in later stages to form a suitable space (FIG. 9J, 9L). None of the crucial material properties were significantly changed by adding COL-I to GM-Ma (FIG. 9M-9P). Ultimately, these results suggested that M-GM provides a suitable environment for MSC-mediated suture regeneration.

To investigate whether the Gli1$^+$ MSCs retained their stemness after 10 days of culture in vitro, a colony-forming assay was performed. Gli1$^+$ MSCs formed colonies (FIG. 9E) and could differentiate towards osteogenic, chondrogenic and adipogenic lineages, confirming their stemness.

Example 3. Suture MSCs in M-GM Support the Regeneration of Cranial Sutures in Twist1$^{+/-}$ Mice To test whether Gli1$^+$ MSCs combined with M-GM can support coronal suture regeneration in Twist1$^{+/-}$ mice with bilateral coronal suture fusion (FIG. 2A, 2C), we generated a rectangular defect 0.3-0.4 mm wide over each of the fused coronal sutures (FIG. 2B, 2D). Gli1+ cells with M-GM (M-GM+SCs) were implanted into the defect on the right side (FIG. 2E, 2F). The defect on the opposite side was either (1) left empty or filled with (2) pure M-GM, (3) suture mesenchymal cells from Gli1-Cre$^{ERT2}$;

ROSA26$^{LoxP-STOP-LoxP-DTA\ GFP}$ mice mixed with M-GM (M-GM+DTA cells), (4) heat-inactivated Gli1+ cells mixed with M-GM (M-GM+H-SCs), or (5) Gli1$^+$ cells mixed with Matrigel (Ma+SCs).

Figure 1:
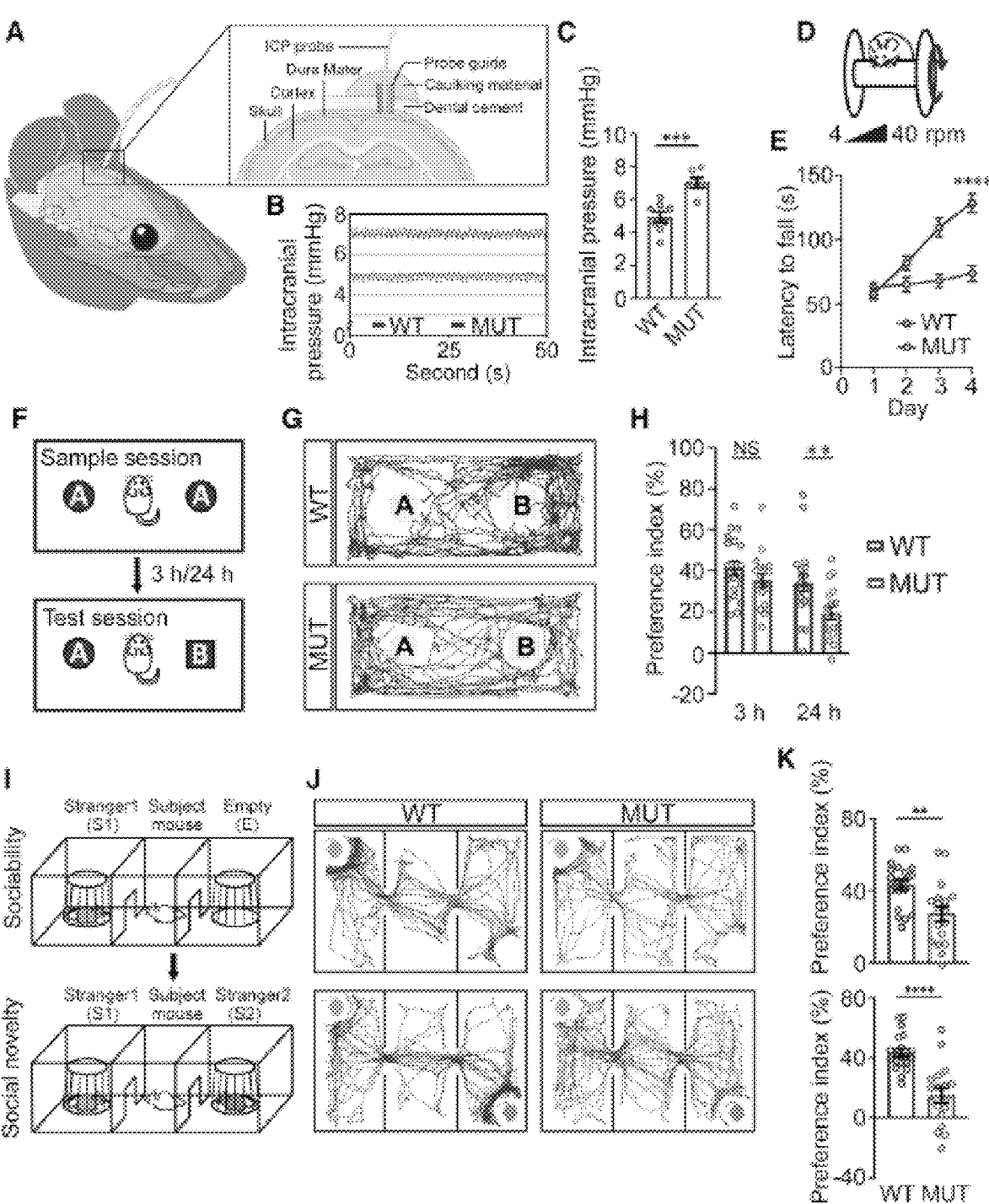
FIG. 1A-K depicts data showing that Twist1$^{+/-}$ mice with craniosynostosis exhibit increased intracranial pressure and cognitive behavioral abnormalities.
Figure 2:
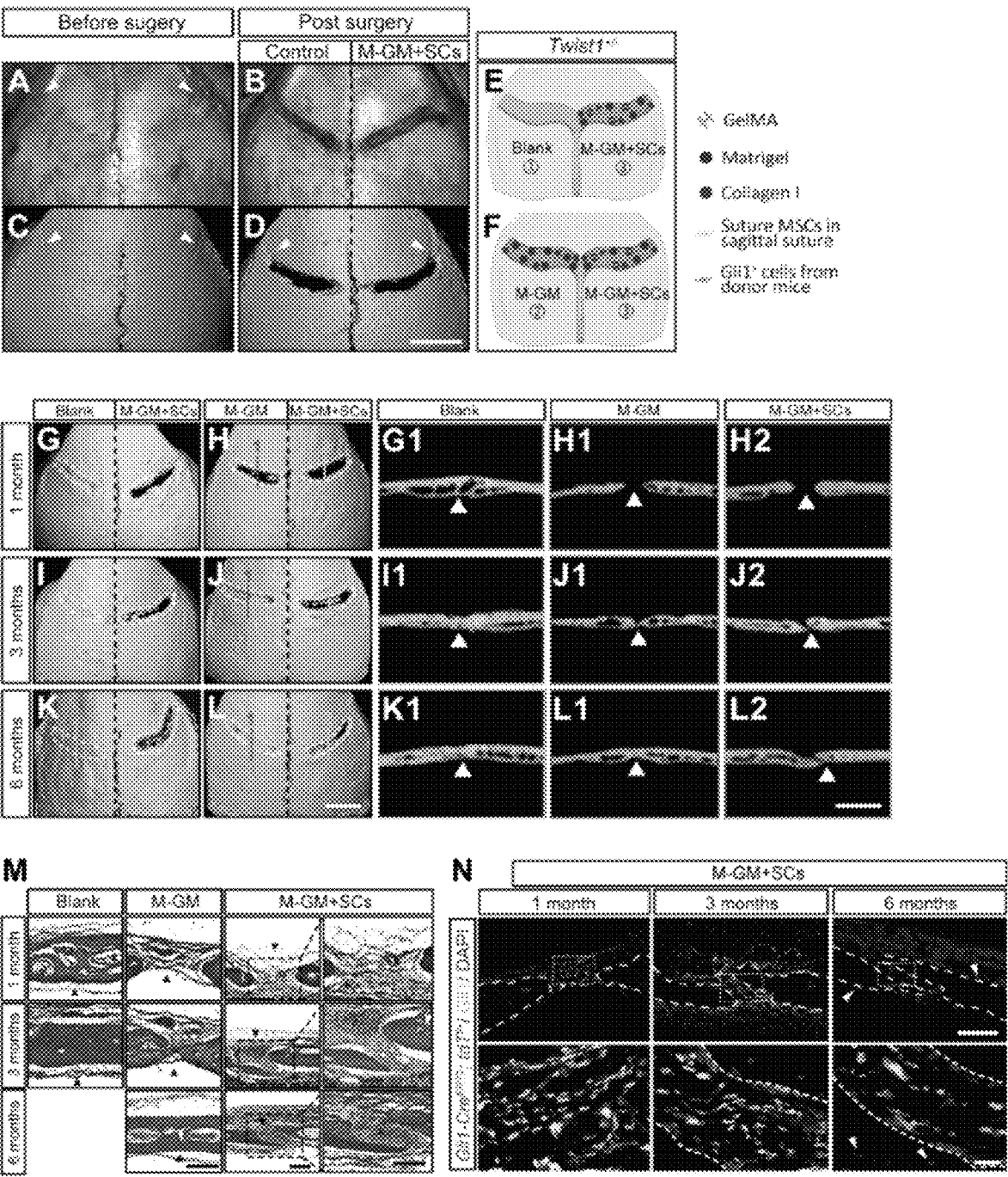

One month after surgery, there was already new bone formation in the blank controls (FIG. 2G, 2G1), whereas spaces were found between the two bones filled with M-GM alone or with M-GM+SCs (FIG. 2H, 2H1, 2H2). The bone matured in the blank controls three months post-surgery (FIG. 2I, 2I1), and the lateral bony edges of defects began to meet in the M-GM group (FIG. 2J, 2J1). In contrast, the bone edges remained separated in the M-GM+SC group (FIG. 2J, 2J2). Six months post-surgery, when the defect was left empty or filled only with M-GM, the suture sites had re-fused (FIG. 2K1, 2L1). At the same time point, the bones were still separated in defects filled with M-GM+SCs (FIG. 2K, 2L). Even after one year, this regenerated suture remained patent (FIG. 10G). All of the other groups experienced resynostosis, including those filled with M-GM+ DTA cells (FIG. 10H), heat-inactivated M-GM+H-SCs (FIG. 10I), and Ma+SCs (FIG. 10J), clearly indicating the crucial roles played by live Gli1$^+$ MSCs cells and M-GM in successful suture regeneration.

Histological analysis (FIG. 2M) confirmed the disappearance of the coronal suture as well as the presence of thicker bone in the empty defects one month post-surgery. In defects filled with M-GM alone, fibrous tissue with some bony islands formed, whereas suture-like tissue could be seen between bone edges in the M-GM+SC group. Three months post-surgery, the porous bone structure of the empty defects was replaced by lamellar bone. The bony margins began to connect in the M-GM group and became thicker six months post-surgery. In the M-GM+SC group, the gap between the bones remained and new fibrous suture formed within six months post-surgery (FIG. 2M).

Next we investigated how implanted Gli1$^+$ MSCs may contribute to suture regeneration in Twist1$^{+/-}$ mice (FIG. 2N). One month post-surgery, the majority of implanted Gli1$^+$ MSCs were present in the center of the defect while a few appeared in the osteogenic fronts, periosteum, and dura (FIG. 2N, left). Interestingly, in defects filled with M-GM+SCs three months post-surgery, large numbers of tdTomato-labeled cells were detectable in the osteogenic fronts, periosteum, and dura mater near the suture (FIG. 2N, middle). A few labeled osteocytes were detected near the osteogenic fronts, while some remained in the center of the regenerated suture. Six months post-surgery (FIG. 2N, right), progeny of implanted Gli1$^+$ MSCs were detectable in the periosteum, dura, and osteocytes of calvaria further away from the defect (white arrowhead), and there were some endogenous Gli1$^+$ MSCs (in green) in the middle of the regenerated suture. Nearly one year post-surgery, the majority of the implanted Gli1$^+$ MSCs took part in the formation of the nearby tissues, with only a few Gli1$^+$ cells remaining in the center of the suture (FIG. 10G). In the defects left empty or filled with M-GM alone, the suture had nearly or totally re-fused, and Runx2$^+$ cells were numerous at all stages (FIG. 10E, 10F). These results suggest that the implanted Gli1$^+$ MSCs in the regenerated suture may contribute to the turnover of the osteogenic fronts, periosteum, and dura to support calvarial tissue homeostasis.

Figure 3:
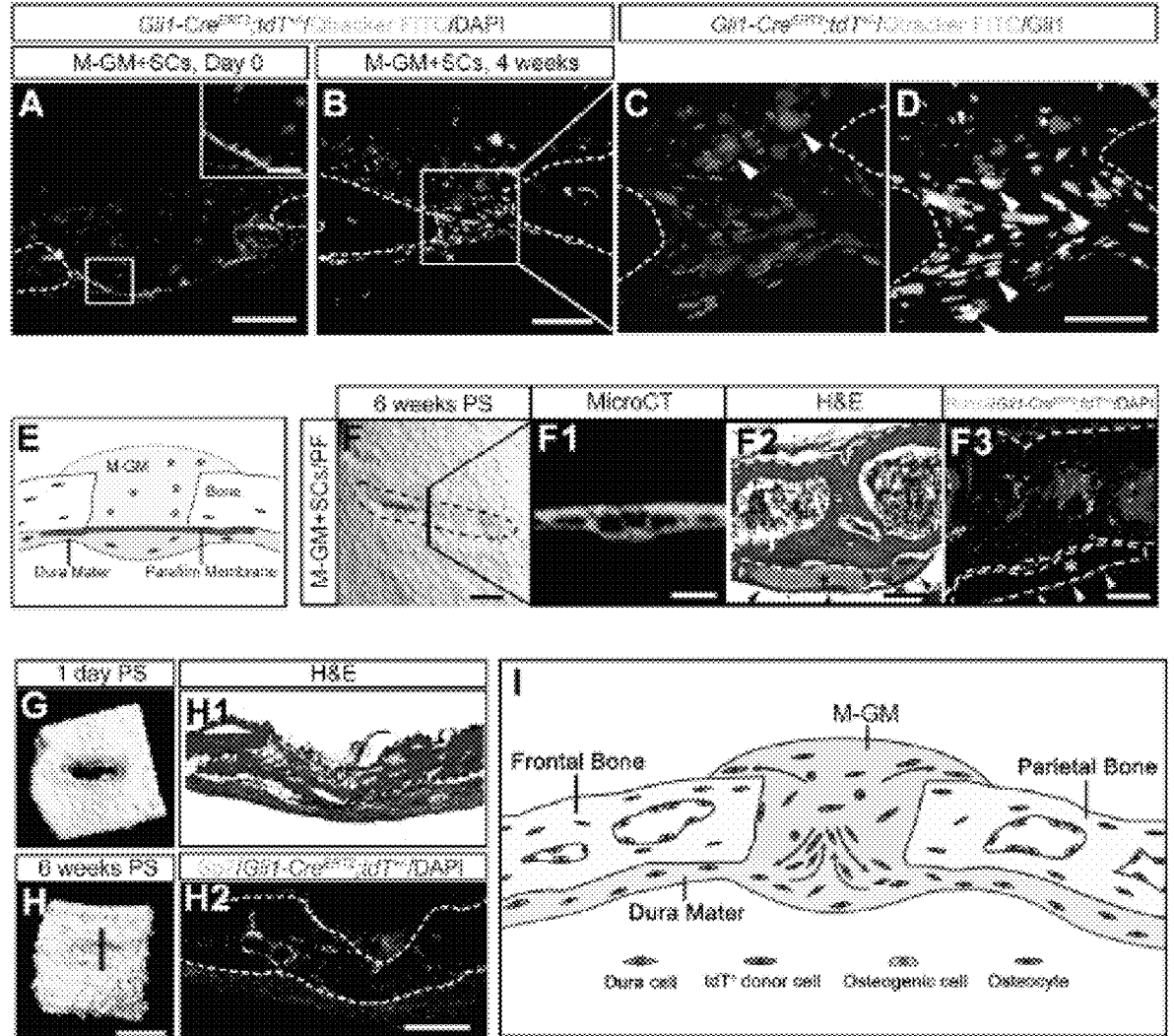
FIG. 3A-I depicts data showing that dura mater cells contribute to the regenerated sutures in Twist1$^{+/-}$ mice.

Example 4. Dura Mater Cells Contribute to Suture Regeneration in Twist1$^{+/-}$ Mice As shown in FIGS. 2N and 10G, some Gli1$^+$ cells (in green) were present in addition to the implanted Gli1$^+$ MSCs (tdTomato$^+$) in the regenerated suture. The ratio of endogenous to implanted labeled cells increased over time, which suggests that the endogenous stem/progenitor cells also played roles in sustaining suture regeneration and function. To investigate the source of these cells, the dura mater under the defect was labeled with FITC prior to the implantation of Gli1+ MSCs and M-GM in Twist1+/− mice with cranio-synostosis (FIG. 3A). Exogenous and endogenous Gli1+ cells were both present in the suture region four weeks post-surgery (FIG. 3B-3D). To confirm whether MSCs from the dura contributed to the newly regenerated suture, a Parafilm membrane with 10 nm pores was placed between the dura and the calvarial bone to block the migration of endogenous MSCs into the suture (FIG. 3E). Six weeks post-surgery, the suture area was almost re-fused in the group with the Parafilm membrane (asterisks in FIG. 3F-3F3), in contrast to the group without the Parafilm membrane, in which the suture space was maintained (FIG. 2). Kidney capsule transplantation of calvarial explants also indicated that M-GM+MSCs cannot regenerate a suture following the removal of the dura. The defect in the explanted bone was filled with bone six weeks post-trans-plantation (FIG. 3G, 3H, 3H1-2). These data clearly suggest that endogenous Gli1+ MSCs, in conjunction with implanted Gli1+ MSCs, help to sustain the regenerated suture in Twist1+/− mice (FIG. 3I).

Although Twist1 is known to maintain cranial suture MSCs and suture patency during embryonic development, its role in regulating postnatal MSCs in the cranial suture remains unclear. To test the functional requirement of Twist in regulating suture MSC fate in adults, we generated GlilCreER;Twist1fl/fl mice. Loss of Twist1 in Gli1+ cells did not lead to craniosynostosis in adult GlilCreER;Twist1fl/fl mice (FIG. 10O, 10P). This suggests that Twist1's postnatal functions are not essential, which may partially explain why implanted Gli1+ MSCs, together with endogenous dura-derived Twist1+/− MSCs, can regenerate a sustainable cra-nial suture and prevent resynostosis in adult Twist1+/− mice.

Example 5. Regenerated Suture Functions Similarly to Natural Cranial Suture

Figure 4:
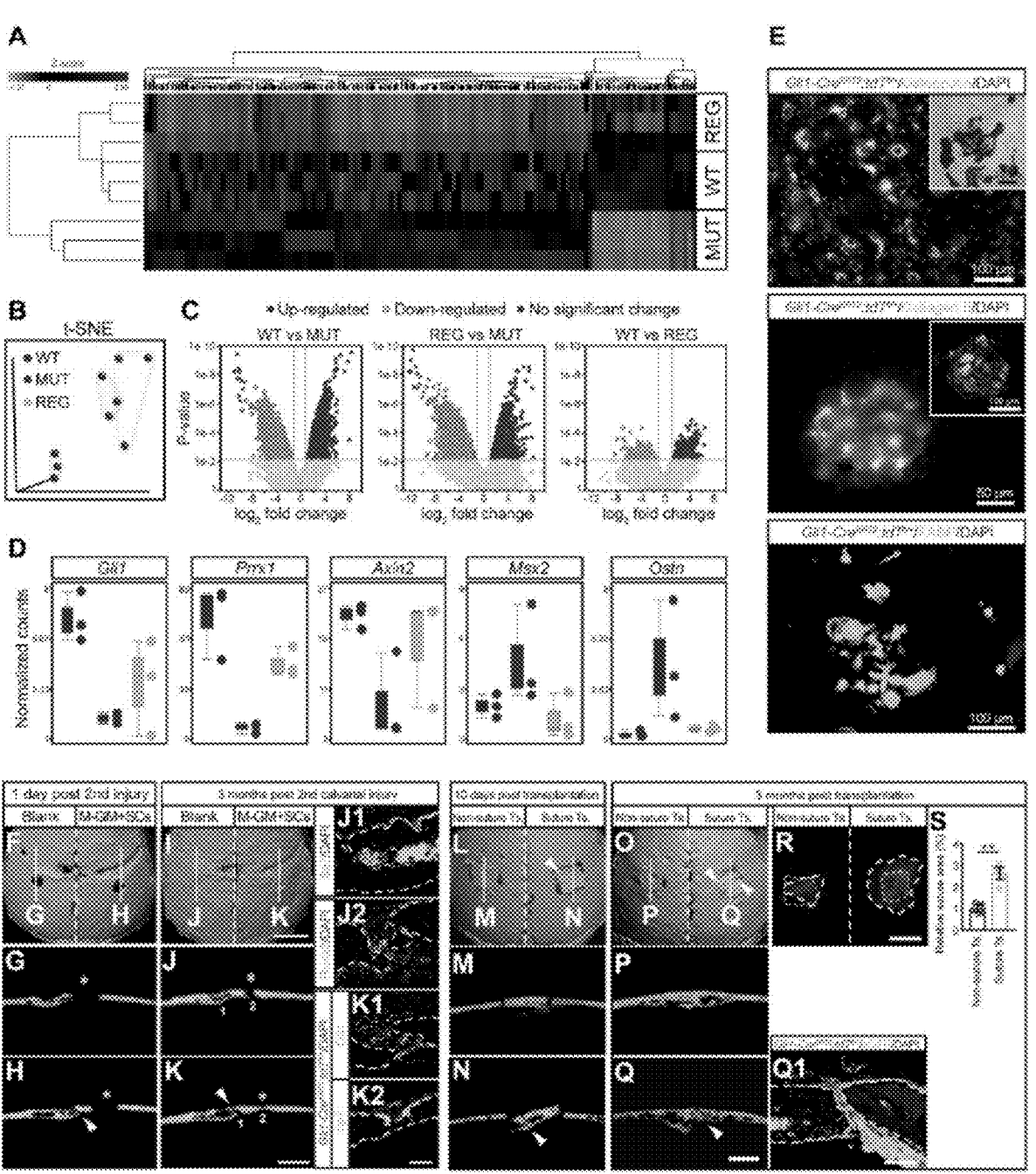

To evaluate how functionally similar coronal sutures regenerated by implanted MSCs and M-GM are to natural sutures, we performed RNA sequencing to compare the gene expression profiles of coronal sutures from WT mice, Twist1+/− mice with bilateral coronal suture fusion (MUT), and the endogenous cells from Twist1+/− mice with regen-erated sutures (REG). The WT and MUT groups had distinct gene expression profiles, while the endogenous cells from the REG group had a gene expression profile more similar to that of a WT coronal suture (FIG. 4A). t-SNE analysis confirmed that the gene distributions of the WT and endog-enous cells from the REG group were closer to each other than to the MUT group (FIG. 4B). The WT group and endogenous cells in the REG group both had ~3000 upregu-lated genes and ~6000 (WT)/~11000 (REG) downregulated genes relative to the MUT group, while there were only 800-900 differentially expressed genes between the WT group and endogenous cells in the REG group (FIG. 4C). Putative marker genes of suture mesenchymal stem/progeni-tor cells such as Gli1, Prrx1, and Axin2 all showed increased expression in the endogenous cells of the REG group in comparison to the MUT group (FIG. 4D). Msx2, a gene implicated in osteogenesis, and Ostn, which is specifically expressed in osteoblasts and osteocytes in adult bone, were both upregulated in the MUT group and restored in the endogenous cells of the REG group compared to the WT group (FIG. 4D). These results suggested that suture regen-eration partially restored the normal suture gene expression profile, and that exogenous MSCs induced endogenous cells from the dura to play an important role in restoring a normal gene expression profile.

To investigate molecular mechanisms underlying suture regeneration, we examined Wnt signaling, which plays an important role in craniosynostosis. Most genes in the Wnt family were upregulated in the MUT group compared to both the endogenous part of the REG group and the WT group (FIG. 11C), including Wnt1, Wnt2, Wnt3, Wnt3a, Wnt5a, Wnt9b, while a few were downregulated in the MUT group, such as Wnt5b, Wnt7b, and Wnt10b. Axin2, a nega-tive regulator of Wnt signaling, was downregulated in Twist1+/− mice, and its expression was reversed by MSC implantation. These results suggest that Twist1+/− cranial sutures exhibited upregulation of Wnt signaling that was reversed by MSC implantation. To examine cellular effects of Wnt signaling upregulation, we assessed the osteogenic differentiation ability of suture mesenchymal cells after treating them with a Wnt activator (Wnt agonist 1) or GSK3 inhibitor (activator of Wnt signaling, LY2090314). Runx2 and OPN expression levels were significantly increased after Wnt signaling was enhanced (FIGS. 11A and 11B). The expression levels of Wnt-related genes could be restored by suture regeneration (FIG. 11C). These results suggested that Wnt signaling upregulation promotes osteogenic differen-tiation of suture mesenchymal cells and contributes to craniosynostosis, all of which were reversed by MSC implantation.

To test the stemness of MSCs in the regenerated cranial suture, we harvested suture mesenchymal cells from coronal sutures six months post-surgery and demonstrated that these cells were capable of osteogenic, chondrogenic, and adipo-genic differentiation (FIG. 4E). Interestingly, the tdTomato-labeled donor cells performed poorly in adipogenic differ-entiation, which implied these cells were more committed towards osteochondrogenic lineages.

To evaluate the ability of the regenerated suture to repair bone after injury, we created a defect in the parietal bone next to the regenerated coronal suture six months after the first surgery (M-GM+SCs group), while on the other side of the calvaria, an identical defect was generated in the parietal bone next to the refused coronal suture (where the defect was left empty) (FIG. 4F-4H). Three months later, both implanted Gli1+ MSCs and endogenous MSCs contributed to the bone regeneration (FIG. 4K1, 4K2). The defects initially treated with M-GM+SCs were completely healed (FIG. 4I and white asterisk in FIG. 4K), whereas the blank controls did not fully heal (white asterisks in FIG. 4J, 4J2). These results suggested that regenerating a suture restores its important ability to support tissue regeneration.

To confirm the regeneration and turnover ability of the regenerated suture, we also transplanted calvarial bone con-taining newly regenerated suture into another Twist1+/− mouse after six months (FIG. 4L, 4N). Calvarial bone with refused sutures taken from the blank control side of Twist1+/ mice with bilateral craniosynostosis was also transplanted as a control (FIG. 4L, 4M). Three months later, transplants containing regenerated suture connected with the host bone (FIG. 4O, 4Q). The newly regenerated tissue grew rapidly and doubled in surface area (FIG. 4Q1, 4R, 4S). In contrast, the transplants without sutures failed to grow and did not connect with the host bone after three months (FIG. 4O, 4P). These results indicated that the regenerated suture possesses the important ability to support calvarial bone turnover and homeostasis.

Figure 5:
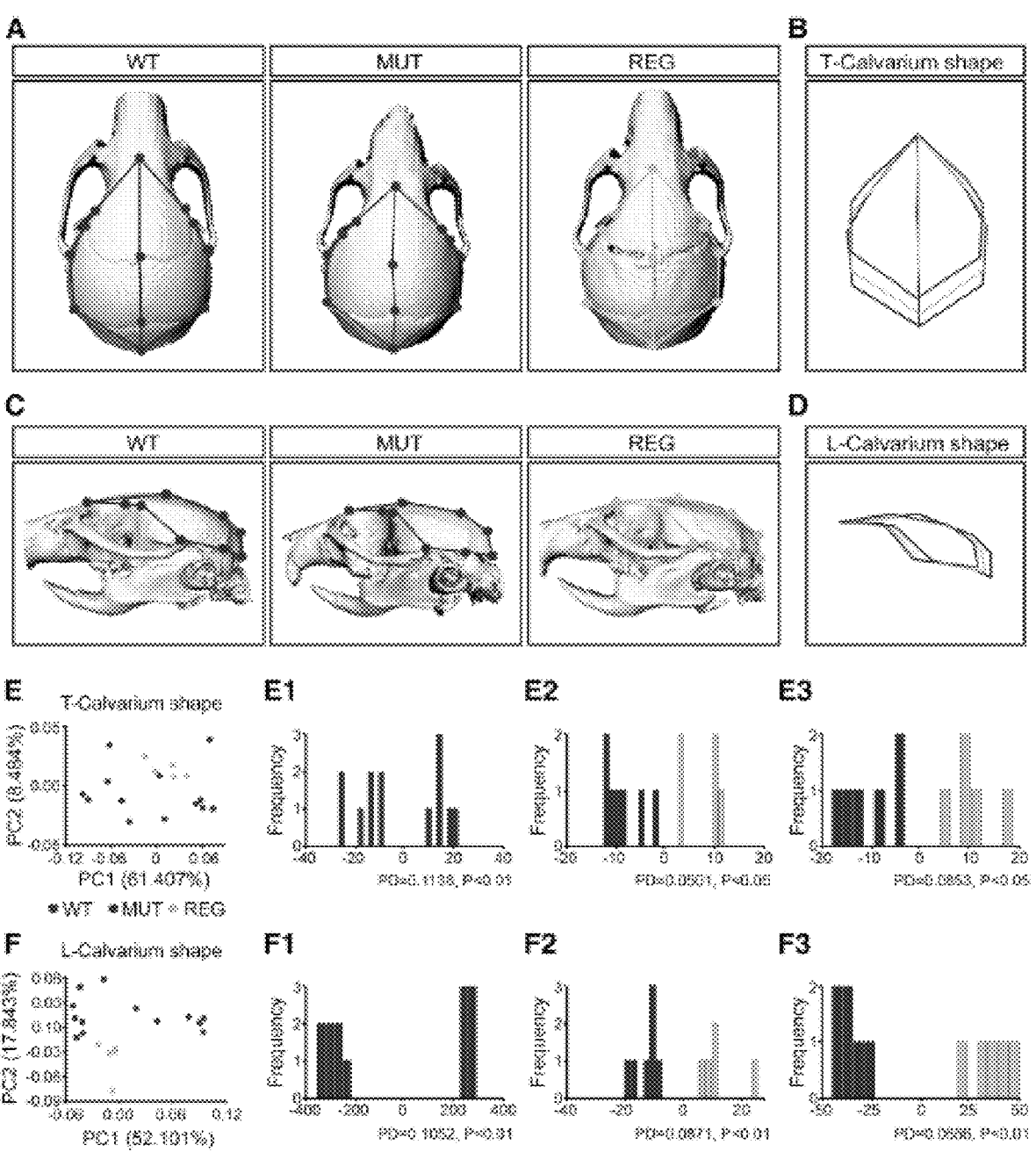
FIG. 5A-F depicts data showing that regenerated sutures rescue skull deformity in Twist1$^{+/-}$ mice with craniosynostosis.

Example 6. Suture Regeneration Rescues Skull Deformity in Twist1$^{+/-}$ Mice To investigate whether regenerating the suture can correct the skull malformations in Twist1$^{+/-}$ mice, we compared the skull shapes of controls (WT), Twist1$^{+/-}$ mice with bilateral coronal suture fusion (MUT), and Twist1$^{+/-}$ mice with bilateral suture regeneration (REG). Established anatomical landmarks (FIG. 11D-11F) were used to analyze the shape of the top of the calvarium (T-calvarium shape, FIG. 5B) and the lateral portion of the calvarium (L-calvarium shape, FIG. 5D) of each group. Skulls of WT control and REG mice were significantly longer in the anterior-posterior direction than those of MUT mice (FIG. 5A, 5C). PCA analysis revealed that the WT and REG groups were more similar to each other than to the MUT group in both T- and L-calvarial shape (FIG. 5E, 5F). Though the REG group had a different T-calvarium shape than WT (FIG. 5E2, Procrustes distance=0.0501; P<0.05), the differences between the MUT and WT/REG groups were greater (FIG. 5E1, Procrustes distance=0.1138; P<0.01, or FIG. 5E3, Procrustes distance=0.0853; P<0.01). The first principal component (PC1) of L-calvarium shape, which accounted for 52.101% of the total variation in the sample, placed the REG mice between the other two groups (FIGS. 5F and 5F1-5F3). These results indicated that suture regeneration partially rescued head shape deformity in Twist1$^{+/-}$ mice with craniosynostosis.

Example 7. Suture Regeneration Improves Neurocognitive Functions in Twist1$^{+/-}$ Mice with Craniosynostosis To test whether suture regeneration rescues neurocognitive dysfunctions in Twist1$^{+/-}$ mice with craniosynostosis, we first created a comparison group by performing bilateral suture regeneration surgery on WT mice on postnatal day 14. The suture structure was recovered at six weeks post-surgery (FIG. 14A) in these mice. We then measured ICP and performed behavioral tests. We did not detect significant changes in ICP (FIG. 14B), social recognition (FIG. 14C-14E), motor learning (FIG. 14F), or anxiety-related behaviors (FIG. 14G, 14H) in recovered WT mice. These results confirmed that the surgical procedure per se does not introduce behavioral changes.

Figure 6:
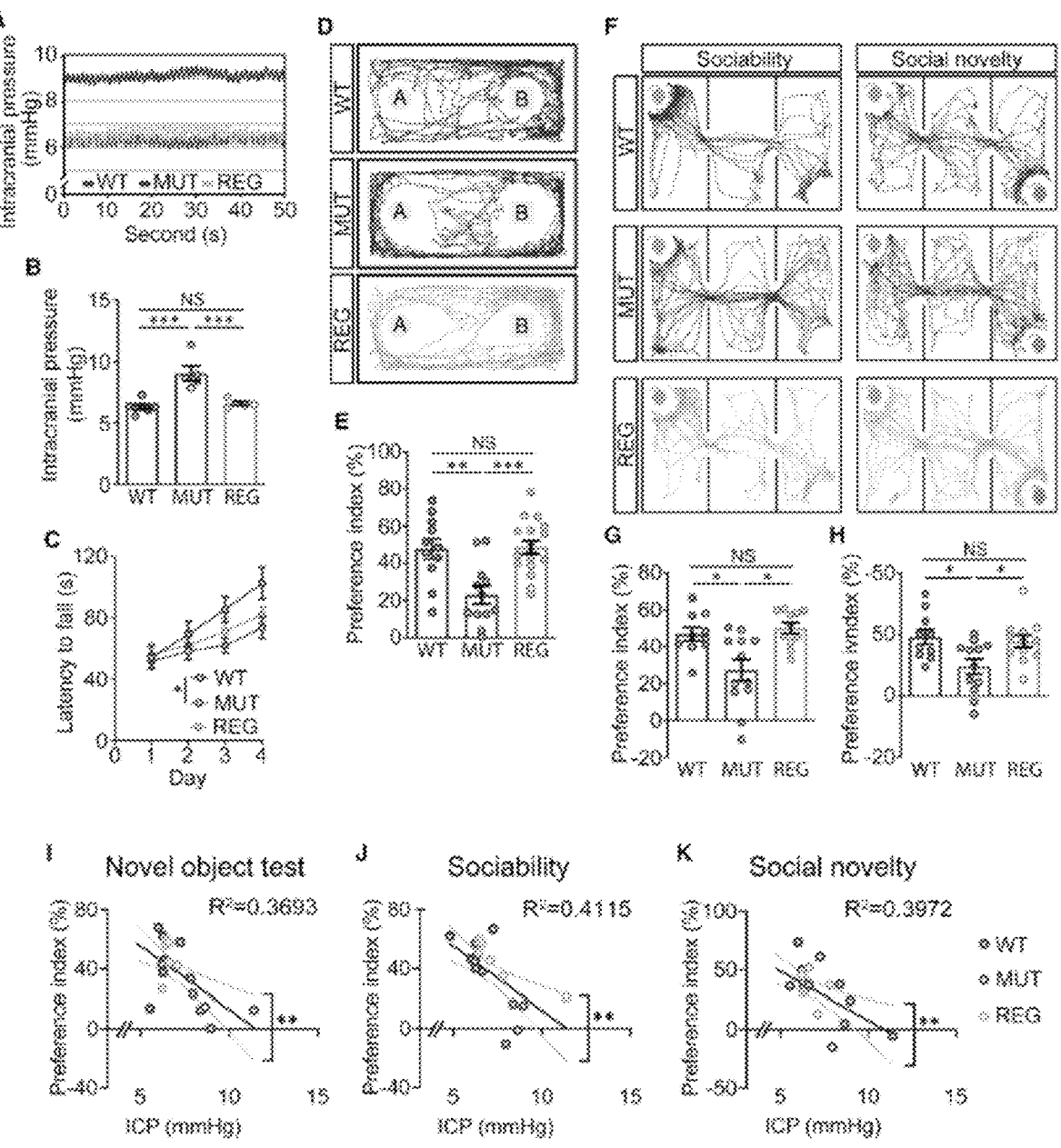
FIG. 6A-K depict data showing that suture regeneration normalizes intracranial pressure and partially restores neurocognitive function in Twist1$^{+/-}$ mice with craniosynostosis.

We next confirmed that elevated ICP in Twist1$^{+/-}$ mice was restored after suture regeneration (FIG. 6A, 6B). We subjected WT and Twist1$^{+/-}$ mice with or without suture regeneration to a battery of behavioral tests. The novel object test revealed that the impaired preference for novel objects in Twist1$^{+/-}$ mice was restored after suture regeneration (FIG. 6D, 6E). The three-chamber test showed that suture regeneration also significantly rescued the sociability and social novelty deficits in Twist1$^{+/-}$ mice (FIG. 6F-6H). Despite a trend towards improvement, motor learning was not significantly rescued after suture regeneration (FIG. 6C). We did not detect changes in general locomotion (FIG. 12A, 12B), grip strength (FIG. 12D) or olfaction (FIG. 12H, 12I), or obvious anxiety-related behaviors (FIG. 12C, 12E-12G).

We performed correlation analyses between ICP and cognitive behaviors, including novel object preference, sociability, and social novelty, which were impaired in Twist1$^{+/-}$ mice. There was a positive correlation between ICP elevation and behavioral deficits, which was reversed by MSC-mediated suture regeneration (FIG. 6I-6K). Together, these results suggested that suture regeneration rescued neurocognitive dysfunctions in Twist1$^{+/-}$ mice, likely through reduction of ICP.

To evaluate the importance of surgery timing, we performed suture regeneration surgery on Twist1$^{+/-}$ mice at postnatal 8 weeks, which corresponds to an adult human ~20 years old. Behavioral studies did not detect significant rescue of neurocognitive deficits when surgery was performed at this later age (FIG. 13A-13F), suggesting the timing of suture regeneration surgery is crucial.

Example 8. Suture Regeneration Restores Brain Volume and Neural Numbers in Twist1$^{+/-}$ Mice With Craniosynostosis In humans, untreated craniosynostosis can lead to microcephaly, correlating with high risk of impaired intelligence, speech and learning as well as behavioral problems. To investigate the mechanisms underlying rescue of neurocognitive functions by suture regeneration, we measured brain volume using magnetic resonance imaging (MRI). Consistent with microcephaly in craniosynostosis patients, whole-brain volume was reduced in Twist1$^{+/-}$ mice with craniosynostosis, but this was reversed by suture regeneration (FIG. 7A-7B). We then examined specific brain regions involved in behaviors altered in Twist1$^{+/-}$ mice with craniosynostosis. The cortical mantle, hippocampus, and corpus callosum volumes were significantly reduced in Twist1$^{+/-}$ mice, and were restored after suture regeneration (FIG. 7A, 7C-7E), while the thalamic volume was not significantly changed in Twist1$^{+/-}$ mice (FIG. 7A, 7F).

To investigate the cellular basis of brain volume changes, we examined neural numbers in different cortical layers, including Cux1-labeled layer II-IV neurons and Ctip2- and Tbr1-labeled layer V-VI neurons. IHC staining showed that Cux1$^{+}$, Ctip2$^{+}$, and Tbr1$^{+}$ neurons were all reduced in Twist1$^{+/-}$ mice (FIG. 7G-7L) and restored after suture regeneration (FIG. 7G-7L). This may indicate restored neurogenesis following suture regeneration in Twist1$^{+/-}$ mice with craniosynostosis, but could also result from reduced cell death. Focusing on the neuronal activation maker c-Fos, we examined prelimbic and perirhinal cortical regions, which are implicated in social and object recognition, respectively. IHC staining showed that the numbers of c-Fos$^{+}$ cells were increased in Twist1$^{+/-}$ mice, and were restored to normal levels after suture regeneration (FIG. 13G). Together, these results suggest that suture regeneration restored neural numbers and brain volume reduced in Twist1$^{+/-}$ mice, providing crucial insights into the mechanisms underlying the impairment and restoration of neurocognitive functions.

Example 9. Materials and Methods

Animals:

Twist1$^{+/-}$ and Twist1$^{fl/fl}$ mice were obtained from Dr. Robert Maxson (University of Southern California). The following strains were purchased from the Jackson Laboratory: Gli1-Cre$^{ERT2}$ (JAX no. 007913), ROSA26$^{LoxP-STOP-LoxP-tdTomato}$ (JAX no. 007905), CAG-EGFP (JAX no. 006567), ROSA26$^{LoxP-STOP-LoxP-eGFP-DTA}$ (JAX no. 006331), and C57BL/6J (JAX no. 000664). For the aged group, mice of both sexes were purchased at about six months of age, and the younger group were two months of age. Mouse experiments were approved by the University of Southern California Institutional Animal Care and Use Committee and performed following the regulations for animal experiments. All mice were housed under a 12 h light/dark cycle in pathogen-free conditions with free access to food and water, in accordance with the Guide for Care and Use of Laboratory Animals of the National Institutes of Health. All mice used in our study were healthy and were not involved in previous procedures. All the mice were identified by ear tags. Ear biopsies were lysed at 55° C. overnight in DirectPCR solution (Viagen, 102-T) followed by 85° C. heat inactivation for 1 hour and PCR-based genotyping (GoTaq Green Master Mix, Promega, and C1000 Touch Cycler, Bio-rad). Mice were euthanized by carbon dioxide overdose and then decapitation.

For all experiments, mice of both sexes were used. For the experiments in FIGS. 1 and 8, two-month-old C57BL/6J mice and Twist1$^{+/-}$ mice were used for ICP and behavioral assays, and one-month-old C57BL/6J mice were used for in situ hybridization of Twist1. For the experiments in FIGS. 2-4 and 9H-9L, 10E-10J, surgeries were performed on Twist1$^{+/-}$ mice with bilateral coronal suture fusion at one month of age. Fusion was assessed prior to surgery by live micro-CT (FIG. 10K-10N). For experiments in FIG. 4F-4K, a second calvarial defect was made on both sides of the parietal bones six months after suture regeneration in the same Twist1$^{+/-}$ mice. For experiments in FIG. 4L-4S, suture and bone transplants were obtained from CAG-GFP; Twist1$^{+/-}$ mice six months after suture regeneration and transplanted into one-month-old Twist1+/mice with bilateral coronal suture fusion. For the experiments in FIGS. 5-7, 12, and 13G, the suture regeneration surgeries were performed on Twist1$^{+/-}$ mice at about two weeks of age after scanning with micro-CT to confirm bilateral coronal suture fusion. For the experiments in FIG. 13A-13F, the suture regeneration surgeries were performed on Twist1$^{+/-}$ mice with bilateral coronal suture fusion at about two months of age. For the experiments in FIG. 14, two-month-old C57BL/6J mice with defect-producing surgeries at two weeks of age were used as the sham-operated group. Cells from one-month-old C57BL/6J mice were used for 2, 3-D culturing (FIG. 9E-9G) and Western blot (FIG. 11A, 11B). One-month-old Gli1-Cre$^{ERT2}$; ROSA26$^{LoxP-STOP-LoxP-tdTomato}$ or Gli1-Cre$^{ERT2}$; ROSA26$^{LoxP-STOP-LoxP-DTA \ GFP}$ mice were used for cell acquisition and surgery one day post-tamoxifen induction (FIG. 10A-10D). For experiments in FIG. 10P, one-month-old Gli1-Cre$^{ERT2}$;Twist1$^{fl/fl}$ mice were induced with tamoxifen and the coronal suture was collected one month post-induction. Tamoxifen (Sigma, T5648) was suspended in corn oil (Sigma, C8267) at 20 mg/ml and 1.5 mg/10 g body weight was injected intraperitoneally (i.p.) daily for 2 days.

Cell Culture, Sorting and Colony-Forming Assay:

The suture mesenchymal cells were harvested as shown in previous studies (James et al., 2008). Briefly, sagittal and coronal sutures of one-month-old wild type, Gli1-Cre$^{ERT2}$; ROSA26$^{LoxP-STOP-LoxP-tdTomato}$ or Gli1-Cre$^{ERT2}$; ROSA26$^{LoxP-STOP-LoxP-eGFP-DTA}$ mice were meticulously excised within 0.5 mm of abutting bones on both sides under a dissecting microscope (Leica, M60), while great care was taken to exclude tissue from the posterofrontal and lambdoid sutures. The overlying periosteum and underlying dura mater were removed carefully. The suture tissues were then washed with PBS and αMEM with 100 U/ml penicillin and 100 μg/ml streptomycin several times and were minced into tiny pieces and transferred into a T25 dish (Nest, 705001) at 37° C. in an atmosphere of 5% carbon dioxide. Our cell culture medium was formulated following an established protocol for mouse MSCs (Liu et al., 2011) and contained αMEM (Gibco, 2065542) supplemented with 20% FBS (Gibco, 2100184), 2 mM L-glutamine (Contained in antibiotics), 55 μM 2-mercaptoethanol (Gibco, 2090354), 100 U/ml penicillin and 100 μg/ml streptomycin (Gibco, 2019321). After 5-6 days, cells were digested with TrypLE (Gibco, 1897328) and the tissues were removed by passing through a 70 μm cell strainer (Falcon, 352350), then the cells were incubated for another 3-4 days before use.

P1 cultured suture mesenchymal cells from Gli1-Cre$^{ERT2}$; ROSA26$^{LoxP-STOP-LoxP-tdTomato}$ mice were dissociated by TrypLE and resuspended in 500-1000 μL medium. Cells were then filtered with a 40 μm cell strainer (Falcon, 352340) to remove the remaining cell mass and sorted for tdTomato$^+$ cells via flow cytometry in a FACS Aria system using FACS Diva software. After sorting, the tdTomato$^+$ cells were centrifuged for colony-forming assay and suture regeneration. After 7 days, the 24-well culture plates (seeded with 2500 tdTomato$^+$ cells/well) were stained overnight with a mixture solution of 0.1% toluidine blue and 2% paraformaldehyde.

Intracranial Pressure Measurement:

Intracranial pressure was measured in two-month-old wild type and Twist1$^{+/-}$ mice with bilateral suture fusion and six months after coronal suture regeneration surgery at two weeks of age or four and a half months after surgery at two months of age. The procedure was performed as described previously (Murtha et al., 2012) with minor modifications. Briefly, mice were anaesthetized with 2% isoflurane and placed in a stereotaxic setup. A hole was drilled into the right parietal bone that was 2 mm lateral and 2 mm posterior from the Bregma. A 10 μl pipette tip (cut to 5 mm in length) used as the sensor guide was inserted into the hole and fixed with dental cement. After the dental cement dried, the sensor guide was filled with sterile PBS and the fiber-optic intracranial pressure probe (FISO Technologies) was inserted until the tip of the probe touched the dura. Caulking material was applied around the probe and the head of the sensor guide to form an airtight seal. Intracranial pressure was recorded with Evolution software (FISO Technologies).

Behavioral Assays:

Behavioral characterization of wild type and Twist1$^{+/-}$ mice with bilateral suture fusion was carried out at 8-12 weeks of age. As for suture regenerated mice, behavioral assays were performed six months after coronal suture regeneration surgery at two weeks of age or four and a half months after surgery at two months of age; age-matched wild type and Twist1$^{+/-}$ mice with bilateral suture fusion were also tested. In all experiments, mice were acclimated to the behavior room at least 60 minutes before the first trial began. Experimenters were blinded to animal genotypes during behavioral tests and data analyses.

Novel object test: This test was performed as described previously (Leger et al., 2013) with minor modifications. Briefly, this test consists of habituation, familiarization, and test phases. In the habituation phase, subject mice were placed in the center of a clean, empty cage and allowed to explore freely for 5 min. After 24 hours, the familiarization phase was performed. Two identical objects were taped to floor along the long axis, 10 cm away from the south and north walls. The mouse was placed in the center of the cage facing the east or west wall and allowed to explore for 10 min. The test phase was performed 3 or 24 hours after the familiarization phase. One of the identical objects was replaced with a novel object with a different shape but similar size. The mouse was placed in the center of the cage facing the east or west wall and allowed to explore for 10 min. The apparatus and objects were thoroughly cleaned with 75% ethanol to remove the olfactory cues between each trial. The entire test phase was videotaped and the travel of the subject mouse was manually documented. The preference index was calculated as $(Tn-Tf)/(Tn+Tf) \times 100\%$, where Tn and Tf represent the time spent exploring novel and familiar objects, respectively.

Three-Chamber Social Interaction Test: The test apparatus was a Plexiglas box containing three compartments connected by small openings that allow the mice free access to each compartment. The subject mouse was first placed in the middle chamber with the side doors closed for 5 min, after which the doors were opened to allow the mouse to explore the three empty chambers. After 10 min of habituation, the mouse was gently guided to the middle chamber and side doors were closed. A stranger mouse was placed in an inverted wire cup in one side chamber and an empty wire cup was placed in the other side chamber. Then the side doors were opened and the subject mouse was allowed to freely explore the chambers for 10 min. After this period, the subject mouse was again guided to the middle chamber and the doors were closed. A second stranger mouse was placed in the previously empty wire cup. The side doors were opened, and the subject mouse was allowed to freely explore for another 10 min. The amount of time that the subject mouse spent sniffing each wire cup was quantified and the preference index was calculated as (Ts1−Te)/(Ts1+Te)× 100% and (Ts2−Ts1)/(Ts2+Ts1)×100%. Here, Te, Ts1 and Ts2 represent the time spent exploring the empty, Stranger 1 and Stranger 2 wire cups, respectively. The apparatus and wire cups were thoroughly cleaned with 75% ethanol to remove the olfactory cues between tests for each mouse.

Rotarod test: The rotarod test consists of training and test phases. Mice were first trained by placing them on a rotating rod (Panlab, Havard Apparatus) at a constant speed of 4 rpm until they were able to stay on the rotating rod for 60 seconds. The test phase was performed 24 hours after the training phase. The rotarod apparatus was set to accelerate from 4 to 40 rpm in 300 seconds, and mice were placed on the rod initially rotating at 4 rpm. The latency (time) to falling off the rod was determined. Each mouse was tested three times a day at 15 min intervals for four consecutive days.

Open field: The subject mouse was placed in an empty arena (40 cm×40 cm) and allowed to freely explore for 15 min. The total traveled distance and time spent in the center zone were recorded and automatically measured using Smart v3.0 (Panlab, Havard Apparatus). The arena was thoroughly cleaned with 75% ethanol between tests for each mouse.

Forelimb grip strength test: This test was performed as described previously (Cabe et al., 1978; Smith et al., 1995). A Grip Strength Meter (Bioseb, BIO-GS3) was used to measure the forelimb grip strength. The gauge was reset and stabilized to 0 g before testing each mouse. A mouse was allowed to grasp the bar mounted on the force gauge and the mouse's tail was slowly pulled back. The peak pull force in grams was recorded on a digital force transducer.

Elevated plus maze test: This test was performed as described previously (Holmes et al., 2002a, 2002b) with minor modifications. Briefly, the elevated plus maze apparatus (Panlab, Havard Apparatus) consisted of two open arms and two closed arms (29.5×6 cm). The entire maze was elevated 40 cm from the floor. Mice were individually placed in the center of the maze, facing towards the open arm, and allowed to freely explore the apparatus for 10 min. The open and closed arm entries (all four paws in an arm) and the time spent in the open arms were recorded using Smart v3.0 (Panlab, Havard Apparatus).

Odor discrimination and habituation test: This test was performed as described previously (Arbuckle et al., 2015) with minor modifications. Each mouse was habituated for one hour to a clean new cage before test. Then the animal was presented five odors in a row delivered on cotton swabs in the following order: water, almond flavor, banana flavor, social odor 1 and social odor 2. The almond and banana odors were prepared by diluting almond and citrus extracts (McCormick) in distilled water (1:100). Each social odor was prepared by wiping a cotton swab for 15 s in a zigzag fashion across the bottom of dirty cage which was used to keep mice of the same sex as the test subject. Each odor was presented three times in a row for 2 min each time with approximately 1 min inter-trial interval. For every non-social odor exposure, the cotton swab was freshly prepared by applying 50 µl of diluted odorant. The cumulative time spent sniffing the odor (the animal's nose was oriented towards the cotton tip at a distance less than 2 cm) was manually recorded.

Gel Synthesis and Testing:

Methacrylated gelatin (GelMA) was synthesized as in the previously described (Van Den Bulcke et al., 2000). Briefly, methacrylic anhydride (MA) was added at a rate of 0.4~0.5 ml/min to a 10% gelatin/PBS (w/v) solution at pH 9 under stirring, to achieve a final MA-to-gelatin ratio of 0.3 ml/g. After allowing the reaction to proceed at 50° C. for 2.5~3 h, the reacted solution was dialyzed against distilled water at 40° C. for 7 days to remove the excessive methacrylic acid and anhydride, then filtered through a 0.22 µm membrane, freeze-dried and stored at −80° C. for later use. The substitution degree of GelMA was measured as described previously (Habeeb, 1966), and was found to be approximately 48%. The freeze-dried GelMA was dissolved in αMEM at 5% (w/v) containing 0.5% (w/v) lithium phenyl-2, 4, 6-trimethylbenzoylphosphinate (LAP) to obtain a solution. The GelMA was modified (creating what we refer to here as modified GelMA, or M-GM) by mixing 5% GelMA solution with Matrigel (Corning, 8015323) and 3 mg/mL collagen I (Gibco, A10483-01) at 4° C. with a volume ratio of 10:2:1. The M-GM solution was cured with a 365 nm UV light source for few seconds to completely crosslink the hydrogels. Concentration-matched (1) pure GelMA, (2) GelMA: Matrigel at a ratio of 5:1 (creating what we refer to here as GM-Ma), (3) GelMA:Matrigel at 2:1, (4) GelMA:Matrigel at 1:1, (5) GelMA:Matrigel at 1:2, and (6) pure Matrigel were also tested.

Mechanical properties: The mechanical properties of gels were characterized by compression and uniaxial tensile tests using a dynamic mechanical analysis instrument (Instron 5542, Instron, Norwood, MA). For unconfined compression tests, the hydrogels were cured in disks (3 mm thick, diameter as 12 mm) by being exposed to 365 nm UV light (1 W/cm$^2$) for 2 min. Each sample was placed between two compression plates and compressed at a displacement rate of 1 mm/min. The samples were cut into 2× 4× 5 mm$^3$ strips after photo-cross-linking and stretched at a rate of 1 mm/min to explore the tensile properties. The compression modulus and Young's modulus were calculated as the slope of the linear region in the 0-10% strain range of the stress-strain curves.

Degradation: The natural degradation properties of the hydrogels were determined in PBS at 37° C. for 1, 2, 3, and 4 weeks. At each time point, remaining hydrogel was washed with distilled water, all liquid was removed and gels were lyophilized. The original dry weight was denoted $W_o$ and the dry weight after incubation was $W_d$. The extent of degradation was determined gravimetrically as the percent weight loss according to following equation: Remaining weight (%)=$(W_o-W_d)/W_d \times 100$.

Diffusion properties: FRAP measurements were performed using confocal laser scanning microscopy (Leica SP8, Germany) to analyze diffusion properties of solutes within the gels as previously reported (Kang et al., 2012; Kaemmerer et al., 2014). Briefly, the gels were loaded with 1 mg/ml FITC-BSA (Invitrogen, A23015). The half time of recovery ($\tau_{1/2}$) and diffusion coefficient were calculated from the experimental recovery curve by fitting of the appropriate FRAP model. All FRAP analyses were performed with MatlabR2019b (Mathworks, Natick, MA, USA). A circular bleach area with a diameter of 50 μm was used throughout all FRAP recordings.

Swelling test: All the gels were photo-cross-linked into a disk shape (thickness=1 mm, diameter=12 mm). Then, the gel disks with different compositions were immersed into 2 ml of PBS at 37° C. for 24 h to reach equilibrium swelling. After being removed from PBS, the gel disks were gently blotted with a Kimwipe to remove the residual liquid, and the swollen weight of each disk was recorded ($W_s$). The samples were subsequently lyophilized and weighed again to determine the dry weight of each disk ($W_d$). The swelling ratio was then calculated as $Q=(W_s-W_d)/W_d$.

Morphology and Viability of Cells in Hydrogels:

To characterize the cell morphology in hydrogels, the P1 cultured suture mesenchymal cells were gently mixed with the hydrogel ($5\times10^5$ cells/ml) until uniform and cured with UV light. After 1 or 5 days, samples were fixed with 2.5% glutaraldehyde overnight, washed with PBS three times and fixed with 1%0.0 for 1 h. After three more washes, they were dehydrated by a graded series of ethanol (30%, 50%, 70%, 80%, 90%, 95%) for 15 min each and 100% ethanol twice for 20 min each, then transferred to isoamyl acetate twice for 15 min each time. Finally, the samples were carefully moved to a critical point dryer (Leica EM CPD300, Germany) for dehydration. The cross-sections of the samples were exposed and coated with Au/Pd using a sputter coater (Leica EM ACE600, Germany), while the morphology of cells inside the hydrogels was observed using scanning electron microscopy (Nova Nano SEM450, FEI, America).

Cellular viability was detected with a live/dead staining kit (Invitrogen, MP 34958). Briefly, suture mesenchymal cells from sagittal and coronal sutures of one-month-old wild type mice were mixed with hydrogel at a density of $5\times10^5$ cells/ml, cured as above, and cultured in αMEM-based medium as described above for 1 or 5 days. Then, the samples were stained with calcein-AM and ethidium homodimer-1 for 30 min. Images were obtained on a Zeiss LSM 710 inverted confocal microscope with a scanning thickness of 3 μm for each layer. The overlaid 2D pictures were analyzed using Leica LAS AF software.

Calvarial Defect Generation:

One-month-old, two-month-old, or two-week-old Twist1$^{+/-}$ mice with bilateral coronal suture fusion were chosen for surgery after confirming the fusion via CT scanning. A midline sagittal incision was made on the calvaria under general anesthesia, and the bilateral coronal sutures and the surrounding bones were exposed by elevating the scalp. The overlying periosteum was removed carefully from the exposed area by curette. Then a dental round burr (Brasseler, H52. 11. 003) was used to create a rectangular defect with 0.3-0.4 mm width by referencing the residual hallmark of the fused suture (white arrowheads in FIG. 2A, 2C, 2D) and the landmark for a normal coronal suture (BRG and SQU in FIG. 11D-11F), while carefully avoiding damage to the underlying dura mater. A strip of bone 0.3-0.4 mm wide was preserved between the defect and the sagittal suture. Three types of cells (tdTomato$^+$ cells, heat-inactivated tdTomato$^+$ cells, and cells from Gli1-Cre$^{ERT2}$; ROSA26$^{LoxP-STOP-LoxP-eGFP-DTA}$ mice) were uniformly mixed with M-GM at a density of $5\times10^7$ cells/ml and 2 μl of the solution was added to the defect. As controls, tdTomato$^+$ cells were mixed with pure GelMA, GM-Ma or Matrigel on ice and then transferred to the defect, or defects were filled with pure M-GM or left empty. All the groups with M-GM were then cured with UV light with a wavelength of 365 nm for a few seconds. The scalp was then sutured closed with 5.0 polyglactin stitches (FIG. 10A-10D).

Suture width: Each calvarial defect was measured six months after surgery to determine the width of the regenerated sutures, and age-matched wild type mice were used as a control. The distance between the two bones was calculated as the width of the suture, and three points along each suture were selected (the most medial, the most lateral and the middle points of each coronal suture). All measurements were included in the analysis.

Dura Mater Blocking:

After a defect of 0.3-0.4 mm width was generated as above, a Parafilm membrane with 10 nm diameter pores (Thermo Fisher Scientific) was carefully placed between the internal surface of calvaria and the dura mater, while carefully avoiding damage to the dura. Then the defects were filled with M-GM+ cells and cured by UV light as outlined above. The calvarial bone together with Parafilm membrane was harvested six weeks later.

Kidney Capsule Transplantation:

We implanted M-GM plus MSCs into the calvarial bone of Twist1$^{+/-}$ mice following the removal of the fused coronal suture. One day after this suture regeneration procedure, we removed a 2 mm×2 mm square area of bone containing M-GM and MSCs. Then we carefully removed the periosteum and dura mater while protecting the M-GM and donor MSCs under a microscope. The explant was then grafted under the kidney capsule of a host mouse as previously described (Xu et al., 2005). The explant was harvested after six weeks.

MicroCt Imaging:

The calvarial bones and kidney capsules containing calvarial explants were radiographed in live mice using a micro-CT (Ct Lab In-vivo 90) device. Images were collected using a 70 KVp and 114 μA X-ray source. All the 3D reconstructions and sections were analyzed using AVIZO 9.4.0 (Thermo Fisher Scientific).

Immunofluorescence Staining and In Situ Hybridization (FISH):

Suture samples were fixed with 4% paraformaldehyde (PFA) in PBS overnight at 4° C., followed by decalcification in EDTA for about 2 weeks, dehydration with a graded sucrose solutions (15% and 30% sucrose for 2 hours each at room temperature, and 30% sucrose with 50% OCT overnight at 4° C.) and immediately embedded in OCT (Sakura Finetek, 4583). Frozen tissue blocks were sectioned at 8 μm on a cryostat (Leica) and mounted on SuperFrost Plus slides (Fisher) for staining.

For brain sample sectioning, animals were intracranially perfused with PBS and 4% PFA, and the brain was dissected out, post-fixed with 4% PFA overnight at 4° C., and dehydrated in 30% sucrose solution for 2 days. The dehydrated samples were embedded in OCT and sectioned at 40 μm on a cryostat (Leica).

Sections were permeabilized with blocking buffer containing 1% BSA, 2% goat serum and 0.3% TritonX-100 in PBS for 1 h at room temperature and then incubated with the following primary antibodies: anti-Gli1 (Novus Biological NBP1-78259, 1:20), anti-Runx2 (Cell signaling technology 12556, 1:100), anti-Sp7 (Abcam ab22552, 1:100), anti-FABP4, anti-Collagen II, anti-Osteopontin (R&D systems SC010, 10 µg/ml), anti-Cux1 (Santa Cruz Biotechnology SC514008, 1:200), anti-Ctip2 (Abcam ab18465, 1:200), anti-Tbr1 (Abcam ab31940, 1:200), or anti-c-Fos (Cell Signaling Technology 2250, 1:400) overnight at 4° C. The following day, sections were incubated with fluorescently conjugated secondary antibodies: Alexa Fluor 488 goat anti-rabbit IgG (Invitrogen A11008, 1:150), Alexa Fluor 488 donkey anti-goat IgG (Invitrogen A32814, 1:150), Alexa Fluor 488 donkey anti-sheep IgG (Invitrogen A11015, 1:150), Alexa Fluor 647 donkey anti-rabbit IgG (Invitrogen A32795, 1:150) or Alexa Fluor 488 goat anti-chicken IgG (Invitrogen A11039, 1:150) together with DAPI (Thermo Fisher Scientific 62248, 1:1000) for 1 h at room temperature and mounted with Vectashield mounting medium (H-1000, Vector Laboratories). Images were captured by a Leica DMI3000 B fluorescence microscope and a Leica DMI6000 CS confocal microscope using Leica LAS AF software.

To observe the source of Gli1$^+$ cells in regenerated sutures, the dura mater right under the coronal suture defect region was labeled very carefully using a Qtracker Cell Labeling kit (Thermo Fisher Scientific, Q25041MP), avoiding surrounding tissues. After staining for 30 min, excess was washed off with PBS, and then the defects were filled with M-GM+MSCs or left empty as mentioned above.

The expression of Twist1 in the brain and coronal suture of one-month-old wild type mice was assayed using an RNAscope 2.5 HD Chromogenic Assay (Single-plex, Advanced Cell Diagnostics). Sections were acquired as mentioned above, after which ISH was performed according to the manufacturer's instructions.

Western Blot Analysis:

Suture mesenchymal cells from one-month-old C57BL/6J mice were cultured with 20 µM Wnt agonist 1 (Selleck, S8178) or 100 nM LY2090314 (Selleck, S7063) for one or two weeks in αMEM. Medium was changed every other day. Total protein was extracted using a solution of loading buffer (Cell Signaling Technology, 7723S), protease inhibitor (Thermo Fisher Scientific, 1861278) and DTT (Cell Signaling Technology, 7723S), then separated by 10% SDS-PAGE and transferred to PVDF membranes (Millipore, ISEQ00005). Membranes were blocked with 5% non-fat dry milk dissolved in TBST for 2 hours at room temperature with gentle shaking, and then incubated with primary antibodies: anti-Runx2 (Cell signaling technology 12556, 1:1000), anti-OPN (Abcam ab63856, 1:500), and anti-βactin (Abcam ab20272, 1:1000) at 4° C. overnight followed by corresponding horseradish-peroxidase (HRP)-conjugated secondary antibodies. Protein expression was detected by Bio-Rad ChemiDoc Touch (Bio-Rad) and intensities of bands were quantitated by Image J software.

RNA Sequencing Analysis:

To determine the differentially expressed genes between seven-month-old C57BL/6J mice (wild type group, WT), seven-month-old Twist1$^{+/-}$ mice (mutant group, MUT), and seven-month-old Twist1+/mice at six months post-surgery (suture regeneration group, REG), RNA sequencing analysis was performed. After removing the periosteum and dura mater, the coronal sutures of WT and REG groups were excised along with less than 0.2 mm of abutting bone on each side under a microscope. A bone sample of the same size was acquired from the coronal suture region of the MUT group. To acquire endogenous cells (tdTomato-negative) from the REG group, 3 mg/ml collagenase type I (Worthington, LS004194) and 4 mg/ml dispaseII (Roche, 04942078001) were used for 1 hour after mincing the regenerated sutures into tiny pieces. Cells were then filtered with a 40 µm cell strainer (Falcon, 352340) to remove the remaining tissue mass and sorted for tdTomato$^-$ cells via flow cytometry in a FACS Aria system using FACS Diva software. RNA was extracted using the RNeasy Micro Kit (Qiagen, 74004). The quality of RNA samples was determined using an Agilent 2100 Bioanalyzer and all groups had RNA integrity (RIN) numbers>7.0. cDNA library preparation and sequencing were performed at the University of California, Los Angeles Technology Center for Genomics & Bioinformatics. The paired-end reads with 1×75 bp read length were generated on NextSeq500 High Output equipment for three pairs from each group. Raw reads were trimmed, aligned using Partek Flow with the mm10 genome, and normalized using RPKM. Differential expression was estimated by selecting transcripts with a significance of $p<0.05$. A two-way hierarchical clustering heat map using Euclidean distance and average linkage was used to display differentially expressed genes from the three groups.

Confirmation of Suture MSC Stemness:

To assay the multipotential differentiation of the regenerated suture cells, cells from Twist1$^{+/-}$ mice were acquired six months after surgery and cultured following the method described for suture MSCs above. After amplification to sufficient density, the cells were seeded into a 24-well culture plate (Corning, CLS3527) or 15 ml conical tube (Thermo fisher, 362695) and analyzed using a functional identification kit for mouse mesenchymal stem cells (R&D systems, SC010) following the manufacturer's instructions. Osteogenic, adipogenic, and chondrogenic differentiation were performed according to the manufacturer's protocol.

Calvarial Injury Model:

A calvarial injury model was established by creating two circular lesions in the parietal bone using a micro-drill; the periosteum was not removed. The lesions were created bilaterally with a size of ~0.8 mm diameter, 1 mm away from the middle of the coronal suture. The left side was left empty to serve as a control while the right side was filled with M-GM plus donor cells six months after the first suture regeneration surgery. Samples were acquired after three months.

Suture Transplantation:

The suture transplantation surgery was performed as described in our previous work (Zhao et al., 2015). Six months after suture regeneration in CAG-EGFP;Twist1$^{+/-}$ mice with bilateral coronal suture fusion, donor mice were euthanized and a 2 mm×2 mm square area of bone containing regenerated suture (or for the control group, an equivalent sample of the coronal suture region) was immediately removed under a microscope and kept on ice for later use. The periosteum and dura mater were carefully preserved. One-month-old Twist1$^{+/-}$ mice with bilateral coronal suture fusion were used as the recipient mice. A midline sagittal incision was made over the calvaria under anesthesia, and the coronal suture region and surrounding bones were exposed by elevating the scalp. The periosteum in the fused suture area was carefully removed and a 2.2-2.5 mm defect was made in the fused coronal suture region of both sides using a dental round burr (Brasseler, H52. 11. 003) without damaging the underlying dura mater. The suture transplant was placed over the recipient calvarial defect with the dura side facing inside. The scalp was then sutured closed with 5.0 polyglactin suture. Samples were acquired three months later.

Craniofacial Shape Analysis:

Discriminant function analysis (DFA) was established for 3 groups using MorphoJ 1.07a (Klingenberg, 2011) referencing previous work (Parsons et al., 2014). The groups compared were WT (6.5-month-old C57BL/6J mice), MUT (6.5-month-old Twist1$^{+/-}$ mice with bilateral coronal suture fusion), and REG (6.5-month-old Twist1$^{+/-}$ mice six months after bilateral suture regeneration). The coordinates of each shape were subjected to Procrustes superimposition to place the landmark configurations into a common space using a standard geometric morphometric approach. Subsets of landmarks were used to individually analyze the differences in shape of two distinct regions of the skull (top of calvarium and lateral portion of calvarium). Principal component analysis was used to identify the variation between different groups in both these distinct regions. The landmark subsets are indicated in FIG. 6A-6C, and the analysis included a 1,000-round permutation test for Procrustes distance.

MRI Analysis:

To determine the global and regional brain volume differences between 6.5-month-old C57BL/6J mice (wild type group, WT), 6.5-month-old Twist1$^{+/-}$ mice (mutant group, MUT), and 6.5-month-old Twist1$^{+/-}$ mice at six months post-surgery (suture regeneration group, REG), all mice were anesthetized with 4% isoflurane and intracardially perfused with 30 ml of 0.1 M PBS containing 10 U/ml heparin (Sigma, H3149) and 2 mM ProHance (a Gadolinium contrast agent), followed by 30 ml of 4% paraformaldehyde (PFA) containing 2 mM ProHance. Then the mice were decapitated, and brains with skulls were incubated in 4% PFA+2 mM ProHance overnight at 4° C. then transferred to 0.1 M PBS containing 2 mM ProHance and 0.02% sodium azide for 10 days before MRI scanning (Gompers et al., 2017). Magnetic resonance images were acquired on a MRSolutions 7 Tesla MRI scanner (Guildford, UK). Three-dimensional anatomical Fast Spin Echo (FSE) images were acquired to encompass the whole brain. Imaging parameters were as follows: TEeffective/TR=26 ms/400 ms, 4 averages, echo train length=4, field of view=16 mm×16 mm×25.6 mm, matrix size=160× 256× 256, and flip angle=90°. Total acquisition time was 280 minutes.

The brain region-of-interest boundaries were manually drawn for each slice using ImageJ and a mouse brain anatomical atlas (Allen Mouse Brain Atlas). The measured areas for the whole brain, cortical mantle, hippocampus, thalamus, corpus callosum, and cerebellum were multiplied by slice thickness to calculate final volumes (mm3).

For all experiments, the number of replicates is stated in the subsection on Quantification and Statistical Analysis (see below) or in the Results section. For sample-size determination, we performed power calculations, in which ap value less than 0.05 was considered as statistically significant difference. For behavioral analyses, based on our preliminary data we determined that the studies required a sample size of n=10 per genotype of each sex.

Inclusion and Exclusion Criteria for Mouse Behavioral Test:

Criteria for exclusion of mice were predetermined. A preliminary observation of general health and home cage behaviors was conducted for each mouse. Preliminary inspections were used to exclude grossly abnormal mice including mice that lie immobile, do not react to action challenges, do not look to be thriving, or are severely ill. In the rotarod test, mice that could not maintain on the rotarod after the training session or jumped and escaped from the rod or testing bench area were excluded from the analysis. In the novel object test, mice that had less than 15 seconds of the total sniffing time for both the familiar and novel object were removed from the analysis. In elevated plus maze, mice that made less than three entries into both open and closed arms or fell off of the maze were removed from the analysis. In the open field, three-chamber and odor discrimination/habituation tests, mice that did not engage in the tested behaviors throughout the entire period of behavioral testing were excluded from the analysis.

Statistics and Reproducibility:

SPSS software version 26.0 was used for statistical analysis. Significance was assessed by using independent two-tailed Student's t-tests or analysis of variance (ANOVA). P values equal to or lower than 0.05 were considered statistically significant.

Data and Code Availability:

RNA sequencing data from seven-month-old control (WT), Twist1$^{+/-}$ mice (MUT), and Twist1$^{+/-}$ mice at six months post-surgery (suture regeneration group, REG) have been deposited at GEO (GSE155562) [NCBI tracking system #21160175].

Any combination of above features, variations, examples, alternatives, or embodiments is within the scope of this disclosure.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described herein without departing from the scope of the claimed subject matter. All such modifications and changes are intended to fall within the scope of the disclosed subject matter.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting.

All references cited herein, including but not limited to published and unpublished applications, patents, and literature references, are incorporated herein by reference for the subject matter referenced, and in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A composition comprising methacrylated gelatin (GelMA), extracellular matrix, collagen I, and Gli1+ mesenchymal stem cells, wherein a volume ratio of GelMA: extracellular matrix:collagen I is about 10:2:1.

2. The composition of claim 1, wherein Gli1+ mesenchymal stem cells are suspended in the composition at a density in a range of $0.1 \times 10^7$ cells/mL to $50 \times 10^7$ cells/mL.

3. The composition of claim 1, wherein GelMA in the composition is at a concentration in a range of 1% w/v to 10% w/v.

4. The composition of claim 2, wherein GelMA in the composition is at a concentration in a range of 1% w/v to 10% w/v.

5. The composition of claim 1, wherein extracellular matrix in the composition is at a concentration in a range of 1% v/v to 30% v/v.

6. The composition of claim 2, wherein extracellular matrix in the composition is at a concentration in a range of 1% v/v to 30% v/v.

7. The composition of claim 3, wherein extracellular matrix in the composition is at a concentration in a range of 1% v/v to 30% v/v.

8. The composition of claim 4, wherein extracellular matrix in the composition is at a concentration in a range of 1% v/v to 30% v/v.

9. The composition of claim 1, wherein collagen I in the composition is at a concentration in a range of 100 μg/mL to 400 μg/mL.

10. The composition claim 2, wherein collagen I in the composition is at a concentration in a range of 100 μg/mL to 400 μg/mL.

11. The composition of claim 3, wherein collagen I in the composition is at a concentration in a range of 100 μg/mL to 400 μg/mL.

12. The composition of claim 4, wherein collagen I in the composition is at a concentration of in a range of 100 μg/mL to 400 μg/mL.

13. The composition of claim 5, wherein collagen I in the composition is at a concentration in a range of 100 μg/mL to 400 μg/mL.

14. The composition of claim 6, wherein collagen I in the composition is at a concentration in a range of 100 μg/mL to 400 μg/mL.

15. The composition of claim 7, wherein collagen I in the composition is at a concentration in a range of 100 μg/mL to 400 μg/mL.

16. The composition of claim 8, wherein collagen I in the composition is at a concentration in a range of 100 μg/mL to 400 μg/mL.

17. A composition comprising methacrylated gelatin (GelMA), extracellular matrix, and collagen I, wherein a volume ratio of GelMA:extracellular matrix:collagen I is about 10:2:1.

18. The composition of claim 17; wherein:

GelMA in the composition is at a concentration in a range of 1% w/v to 10% w/v; and extracellular matrix in the composition is at a concentration in a range of 1% v/v to 30% v/v; and collagen I in the composition is at a concentration in a range of 100 μg/mL to 400 μg/mL.

19. The composition of claim 1, wherein Gli1+ mesenchymal stem cells are suspended in the composition at a density of about $5 \times 10^7$ cells/mL.

20. The composition of claim 1, wherein extracellular matrix in the composition is at a concentration in a range of about 15% v/v.

* * * * *